United States Patent
Sun et al.

(10) Patent No.: US 10,882,853 B2
(45) Date of Patent: Jan. 5, 2021

(54) TYROSINE KINASE INHIBITOR AND APPLICATION THEREOF

(71) Applicant: LaNova Medicines Limited, Shanghai (CN)

(72) Inventors: Fang Sun, Shanghai (CN); Youni Zhan, Shanghai (CN)

(73) Assignee: LaNova Medicines Limited, Shanghai (CN)

( * ) Notice: Subject to any disclaimer, the term of this patent is extended or adjusted under 35 U.S.C. 154(b) by 0 days.

(21) Appl. No.: 16/333,050

(22) PCT Filed: Jun. 22, 2017

(86) PCT No.: PCT/CN2017/089501
§ 371 (c)(1),
(2) Date: Mar. 13, 2019

(87) PCT Pub. No.: WO2018/049861
PCT Pub. Date: Mar. 22, 2018

(65) Prior Publication Data
US 2019/0248772 A1  Aug. 15, 2019

(30) Foreign Application Priority Data

Sep. 13, 2016  (CN) .......................... 2016 1 0822529

(51) Int. Cl.
| | |
|---|---|
| *C07D 413/12* | (2006.01) |
| *C07D 413/14* | (2006.01) |
| *A61P 29/00* | (2006.01) |
| *A61P 35/00* | (2006.01) |
| *A61K 31/5377* | (2006.01) |
| *C07D 401/04* | (2006.01) |

(Continued)

(52) U.S. Cl.
CPC ........ *C07D 413/12* (2013.01); *A61K 31/5377* (2013.01); *A61P 29/00* (2018.01); *A61P 35/00* (2018.01); *C07D 215/22* (2013.01); *C07D 401/04* (2013.01); *C07D 401/12* (2013.01); *C07D 413/14* (2013.01)

(58) Field of Classification Search
CPC .. C07D 413/12; C07D 215/22; C07D 413/14; C07D 401/04; A61K 31/5377; A61P 29/00; A61P 35/00
See application file for complete search history.

(56) References Cited

FOREIGN PATENT DOCUMENTS

| WO | WO 2005/030140 | * | 4/2005 |
| WO | 2010045095 A1 | | 4/2010 |

OTHER PUBLICATIONS

Pearce et al., Failure modes in anticancer drug discovery and development, Cancer Drug Design and Discovery Edited by Stephen Neidle, Chapter 18, pp. 424-435 (2008).*

(Continued)

*Primary Examiner* — Deepak R Rao
(74) *Attorney, Agent, or Firm* — Ice Miller LLP

(57) ABSTRACT

The invention discloses a compound with the following formula (I), wherein, K is selected from: cycloalkyl

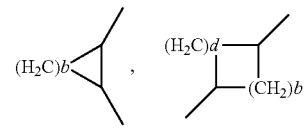

and halo alkyl

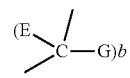

or N—R6. The invention also discloses a tyrosine kinase inhibitor containing the above compound and the use of the compound in preparing drugs for treating cancers. The tyrosine kinase inhibitor of the invention can inhibit the bioactivity of multiple signal conduction kinases such as C-MET, VEGF, KDR, etc., can effectively inhibit cell proliferation and has favorable therapeutic effects on various diseases such as cancer. In particular, the present invention has significant therapeutic effects especially on lung cancer, gastric cancer, ovarian cancer, malignant glioma, etc., and has a very broad application prospect.

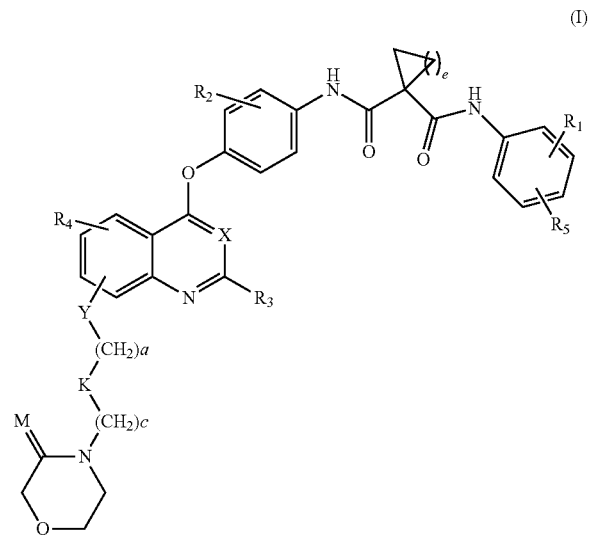

10 Claims, 4 Drawing Sheets

(51) Int. Cl.
    *C07D 401/12*     (2006.01)
    *C07D 215/22*     (2006.01)

(56)     References Cited

OTHER PUBLICATIONS

Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Acute Leukemia, Merck Manual (Online Edition) 6 pages, pp. 1-6 (2013).*
Hanks et al., The eukaryotic protein kinase superfamily: kinase (catalytic) domain structure and classification, Protein Kinases 6, The FASEB Journal, vol. 9, No. 8, pp. 576-596 (1995).*
International Preliminary Report on Patentability dated Mar. 19, 2019 in International Application No. PCT/CN2017/089501; dated Mar. 28, 2019.
International Search Report dated Sep. 26, 2017 in International Application No. PCT/CN2017/089501.

* cited by examiner

Foretinib

Compound 10

Internal reference SCR-1510

Foretinib

Compound 10

Compound 5

TYROSINE KINASE INHIBITOR AND APPLICATION THEREOF

CROSS-REFERENCE TO RELATED APPLICATION

This application is a Section 371 of International Application No. PCT/CN2017/089501, filed Jun. 22, 2017, which was published in the Chinese language on Mar. 22, 2018, under International Publication No. WO 2018/049861 A1, which claims priority under 35 U.S.C. § 119(b) to Chinese Patent Application No. 201610822529.0, filed on Sep. 13, 2016, the disclosures of which are incorporated herein by reference in their entireties.

FIELD OF THE INVENTION

The invention relates to the technical field of medicine, in particular to a tyrosine kinase inhibitor and the use thereof.

BACKGROUND OF THE INVENTION

Protein kinase is a phosphotransferase that transfers the gamma phosphate ester group of adenosine triphosphate (ATP) to a specific amino acid residue, in order to achieve protein phosphorylation and thereby achieve its physiological and biochemical functions.

Protein kinase has an important function in information conduction. Abnormal protein kinase cannot perform normal signal transmission and may cause pathological changes, such as pathological state of protein kinases, such as tumor cell proliferation, cell death, inflammation, cardiovascular disease, etc. Protein kinase is mainly divided into two categories: protein tyrosine kinase (PTKs) and receptor tyrosine kinase (RTKs). ROS1/C-MET in the MET protein kinase is an important subline of RTPs, and it is also known as hHGFR and RON; ROS1/C-MET can play an important role in the growth and metabolism of tumor initiating cells, and it is the target for clinical researches on multiple drugs.

Therefore, ROS1/C-MET kinase inhibitors, especially tyrosine kinase inhibitors of micromolecular compounds, are urgently needed in the field of biomedical technology.

SUMMARY OF THE INVENTION

The technical problem to be solved for the invention is to provide a tyrosine kinase inhibitor, the kinase inhibitor can inhibit the activity of multiple tyrosine kinases involved in signal conduction, such as C-MET, VEGF, KDR, RON, KIT, PDGF, FGF, SRC, etc., and it can effectively inhibit the proliferation of tumor cells to get better therapeutic effect on cancers in clinic.

In order to solve the above technical problem, the invention is implemented by the following technical solution:

On one aspect of the invention, it provides a compound with the formula (I)

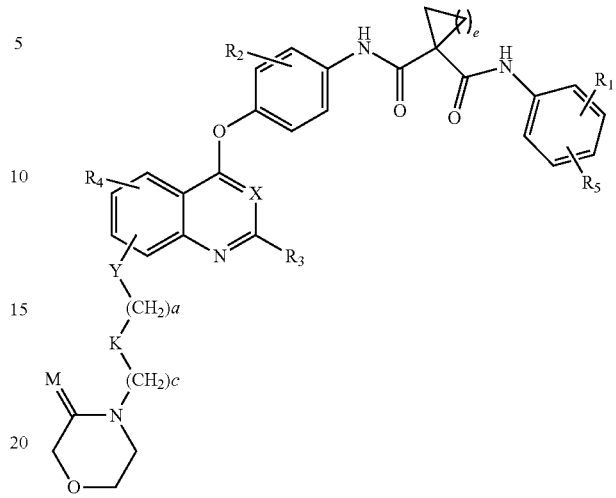

or its pharmaceutically acceptable salts thereof, wherein,

K is selected from the following groups: cycloalkyl

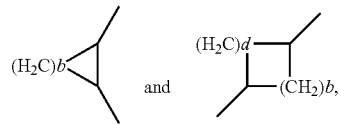

halo alkyl

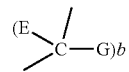

or N—R6; b and d are 1, 2, 3 or 4; E and G are one of hydrogen, halogen, hydroxy, alkoxy, ketone, sulfydryl and alkyl sulfydryl, but E and G cannot be hydrogen at the same time; R6 is one of hydrogen, lower halo alkyl, lower halogenated cycloalkyl, lower alkyl and lower cycloalkyl;

R1, R2, R3, R4 and R5 are one or more of hydrogen, halogen, lower halo alkyl, lower halogenated cycloalkyl, lower alkyl, lower cycloalkyl, hydroxy, lower alkoxy, lower cycloalkoxy, lower alkenyl and lower alkynyl, respectively;

X is one of C—R, C—(CN) and N, and R is one of hydrogen, halogen, lower halo alkyl, lower halogenated cycloalkyl, lower alkyl, lower cycloalkyl, hydroxy, lower alkoxy, lower cycloalkoxy, lower alkenyl and lower alkynyl;

Y is one of O, S and N—R6 or is null, and M is O or null;

a and c represent a number of 0, 1, 2 or 3, respectively; e is a number of 1 or 2.

Preferably, at least one of E and G is halogen F.

Preferably, Y is O or null.

Preferably, the compounds with the formula (I) comprise the compounds in the following specific structures:
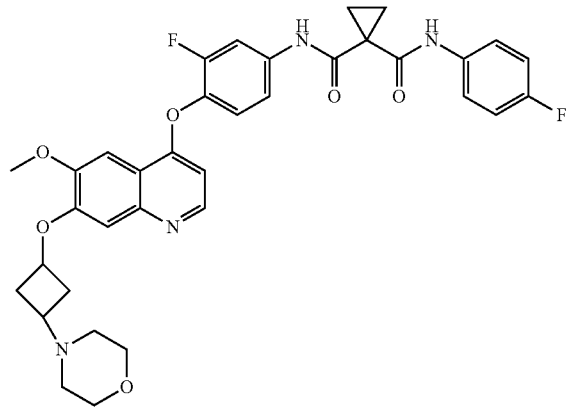
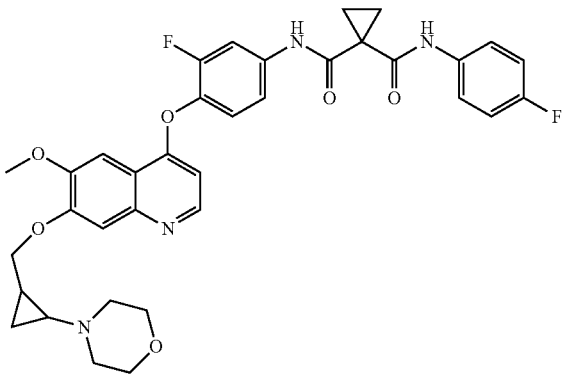
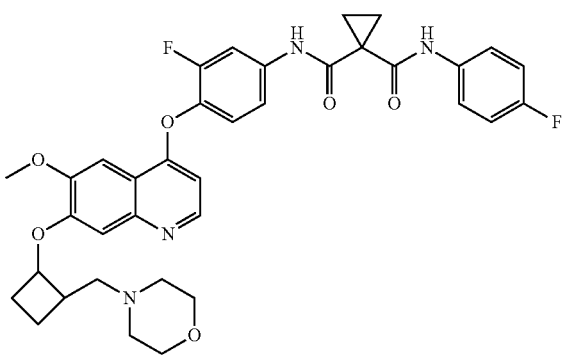
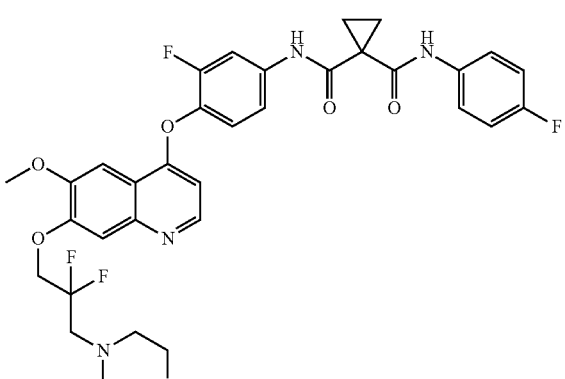
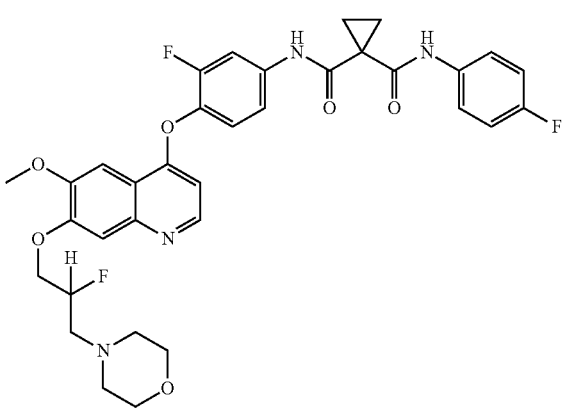

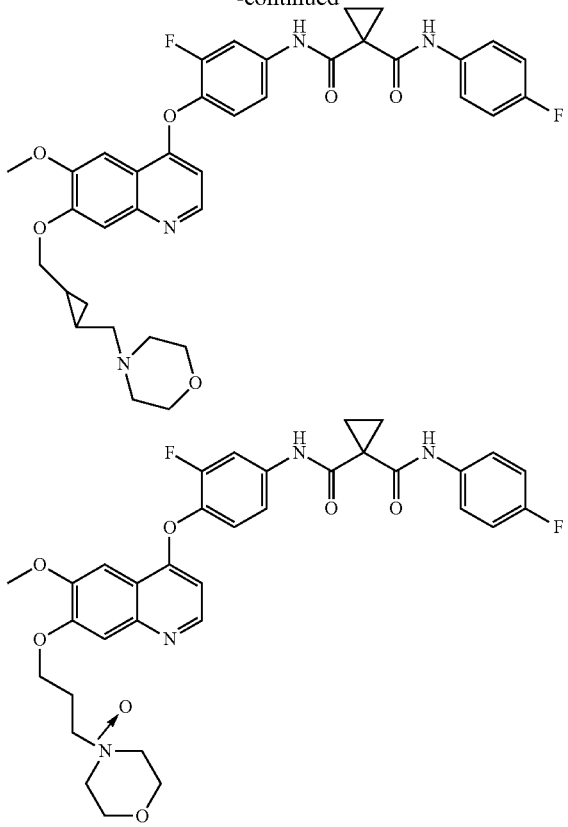
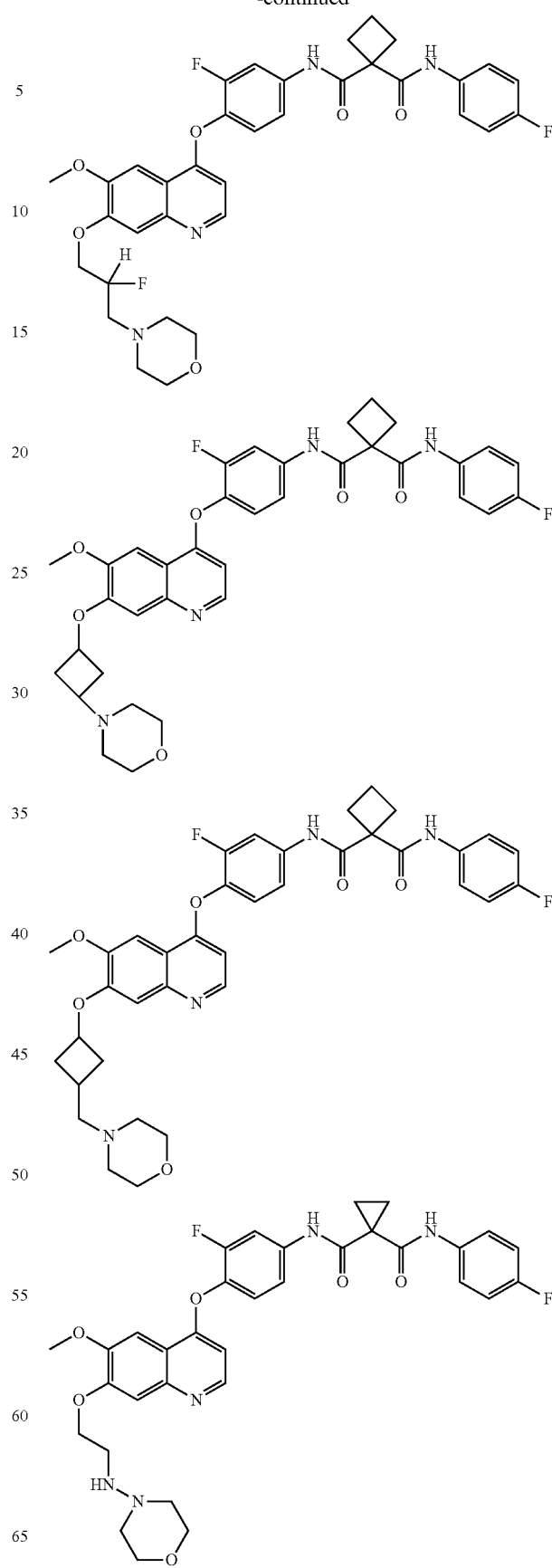

7
-continued
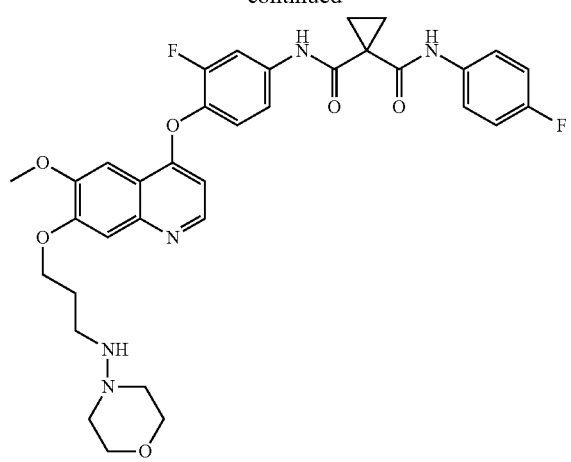
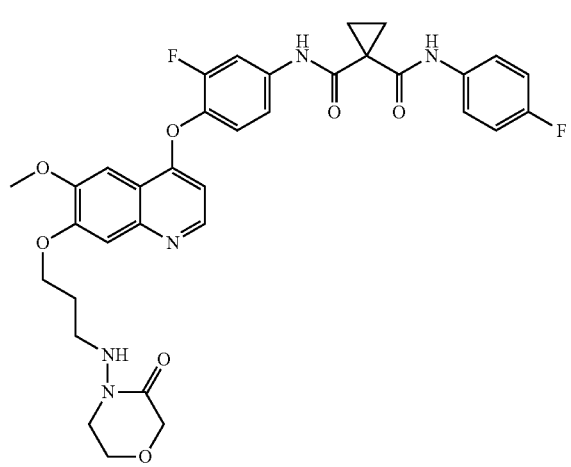
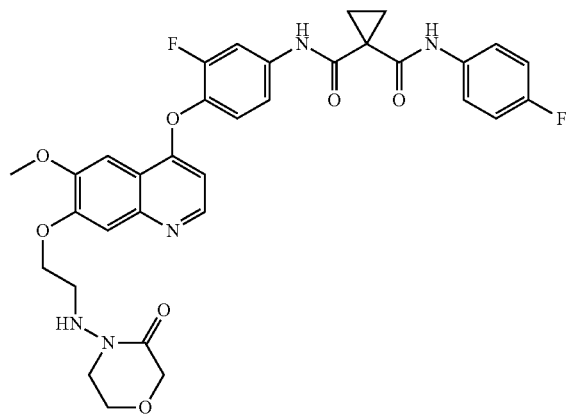
8
-continued
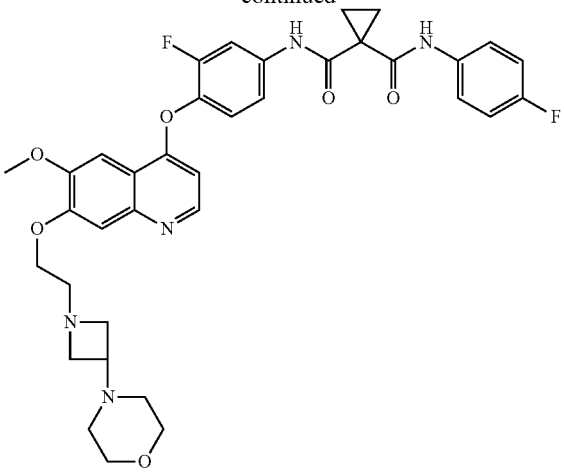
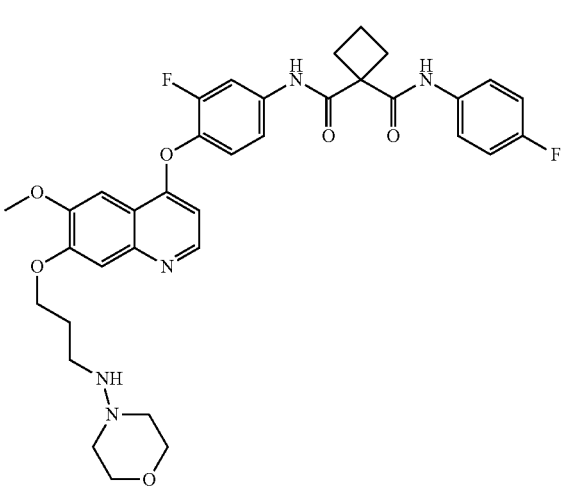
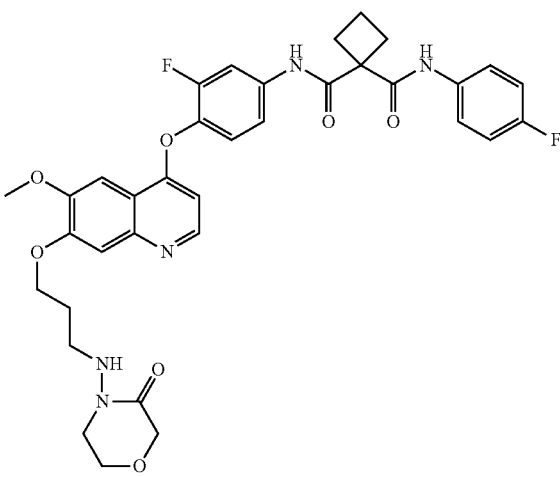

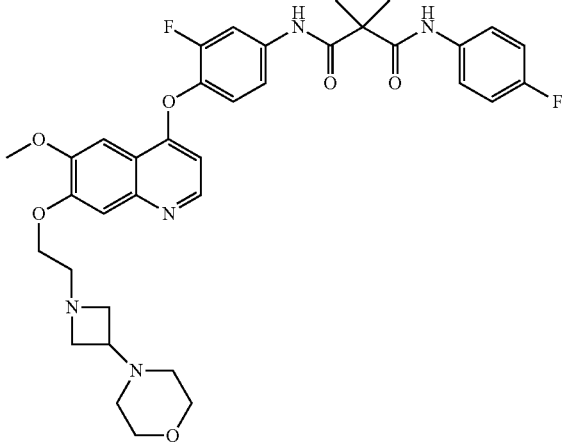

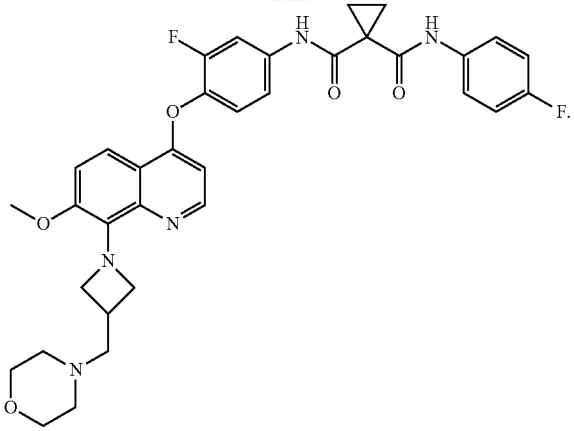

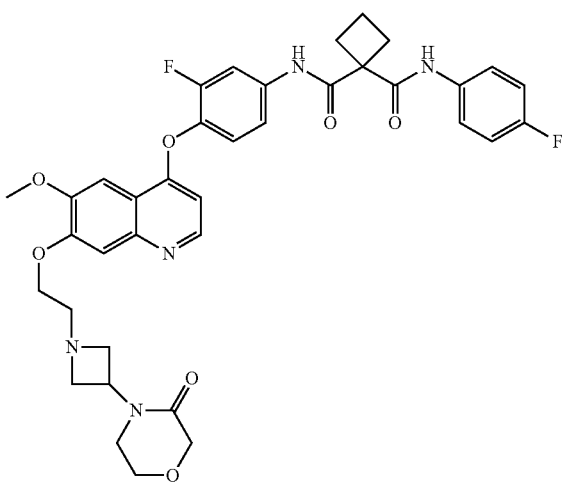

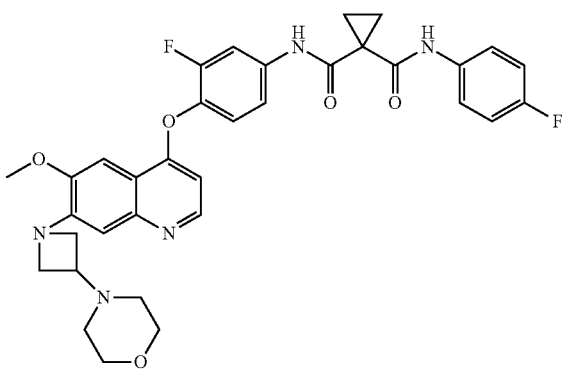

On another aspect of the invention, it also provides a pharmaceutical composition, and the composition comprises a safe and effective amount of the above compound and a pharmaceutically acceptable carrier.

The above acceptable carrier is nontoxic and can be used for auxiliary application without adverse effect on the therapeutic effect of the compound. Such carrier can be any commonly available solid excipient, liquid excipient, semi-solid excipient or gas excipient in aerosol composition for those skilled in the art. Solid drug excipients include starch, cellulose, talc, glucose, lactose, sucrose, gelatin, malt, rice, flour, chalk, silica gel, magnesium stearate, sodium stearate, glyceryl stearyl ester, sodium chloride, anhydrous skim milk, etc. Liquid and semi-solid excipients can be selected from glycerin, propylene glycol, water, ethanol and various oils, including the oil originated from petroleum, animal and plant or synthetic oil, such as peanut oil, soybean oil, mineral oil, sesame oil, etc. Preferable liquid carriers, especially those used for injectable solutions, include, water, saline, glucose aqueous solution and glycol. In addition, other adjuvants such as flavoring agent, sweetening agent, etc. can also be added in the composition.

The compound of the invention can be administrated in the therapeutic effective dose, it can be administrated either orally or systemic (such as transcutaneously, nasal inhalation or suppository) or parenterally (such as intramuscularly, intravenously or subcutaneously). Oral administration is preferred, and it can be adjusted according to the severity of disease.

The actual application amount (i.e., active ingredient) for the compound of the invention depends on multiple factors, such as the severity of disease to be treated, the age and relative health level of the treated subject, the efficacy of the used compound, way and form of administration, and other factors.

Various dosage forms of the medicinal composition of the invention can be prepared in accordance with the conventional methods in the field of pharmacy. For example, the compound can be mixed with one or more carriers, and then it was prepared into the desired dosage form, such as tablets, pills, capsules, semi solid, powder, slow release formulation, solution, suspension, compounding solvent, aerosol, etc.

On another aspect of the invention, it also provides a tyrosine kinase inhibitor containing the above compound.

The tyrosine kinase comprises the kinases of C-MET, VEGF, KDR, RON, KIT, PDGF, FGF and SRC.

On another aspect of the invention, it also provides the use of the above compound in preparing drugs for treating cancers.

Tyrosine kinase is a target with obvious effect for anti-tumor drugs, whereas the compound of the invention has significant activity in inhibiting tyrosine kinase, experiments have confirmed that these compounds have inhibitory effect on the proliferation of various cancer cells, and thus the compound of the invention is applicable for treating various cancers. Especially, it has better therapeutic effects on lung cancer, gastric cancer, ovarian cancer, colon cancer and malignant glioma.

On another aspect of the invention, it also provides the use of the above compound in preparing drugs for treating inflammations.

The compound of the invention and each of multiple signal conduction kinases such as C-MET, VEGF, KDR, RON, KIT, PDGF, FGF, SRC, etc. have favorable bioactivity and are associated with multiple signal conduction pathways, and thus they have therapeutic effects on various diseases, such as cancer, inflammation, lymphedema, diabetes mellitus, etc.

The tyrosine kinase inhibitor of the invention can inhibit the bioactivity of multiple signal conduction kinases such as C-MET, VEGF, KDR, etc., and can effectively inhibit cell proliferation and has favorable therapeutic effects on various diseases such as cancer. In particular, the present invention has significant therapeutic effects especially on lung cancer, gastric cancer, ovarian cancer, malignant glioma, etc., and has a very broad application prospect.

BRIEF DESCRIPTION OF DRAWINGS

The invention will be further explained in details by combining with the drawings and embodiments.

DETAILED DESCRIPTION OF THE INVENTION

Figure 1:
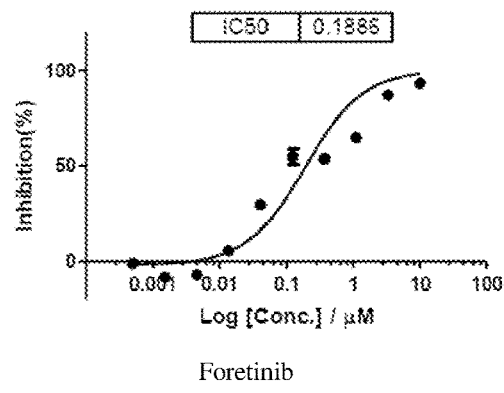
FIG. 1 is the fitted curve for the inhabitation on the proliferation of human lung adenocarcinoma cells HCC78 in Example 10 of the invention.
Figure 1:
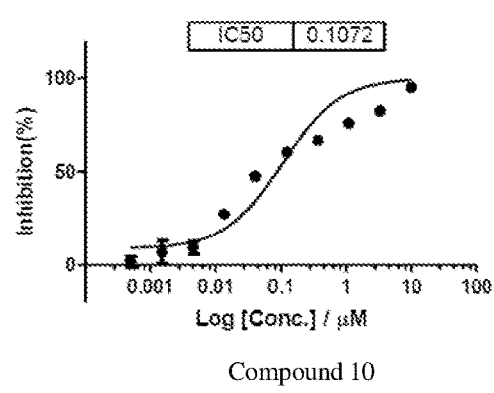
Figure 1:
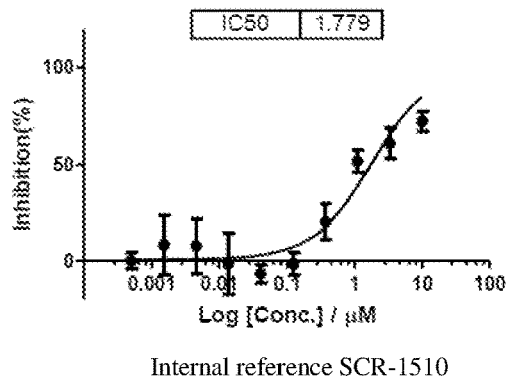

Example 1 Synthesis of Tyrosine Kinase Inhibitor Compound 24

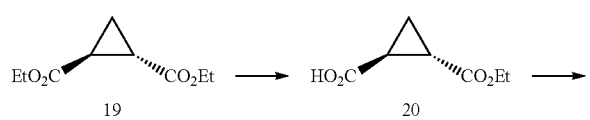

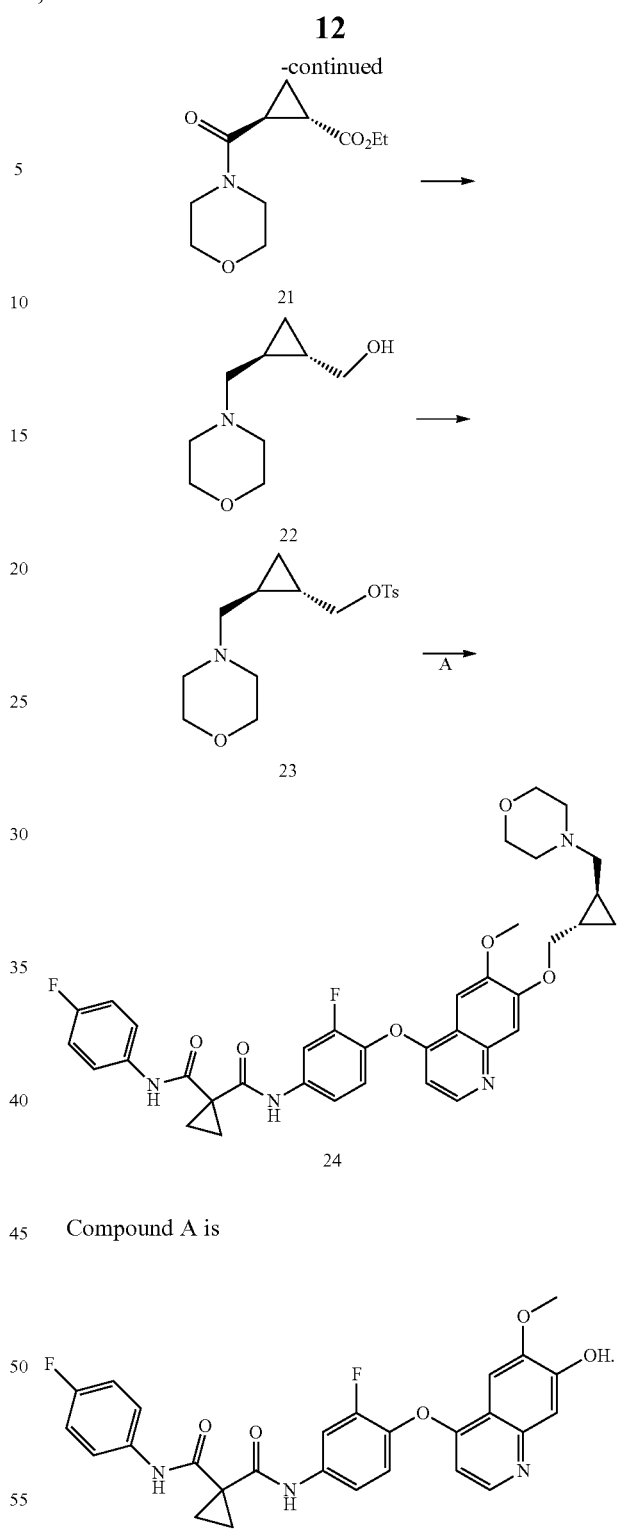

Compound A is

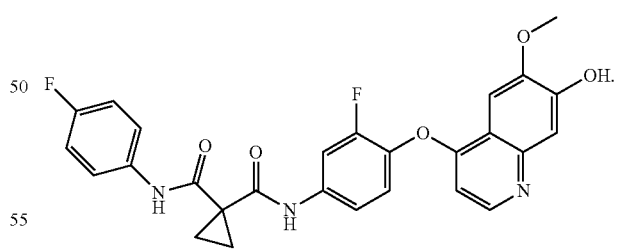

The method includes the following steps:

Step 1, 1.3 g, 7 mmol of Compound 19 was dissolved in 50 ml of methalnol. Compound 19 is diethyl trans-1,2-cyclopropanedicarboxylate. Then 1N of 1 mol/L NaOH solution was added into the above solution, and stirred at room temperature overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; after drying by distillation, the above organic phase concentrated and dried by distillation was purified using column chromatography on silica gel, so as to obtain 1 g of yellow oil 20 with a yield of 77%; Compound 20 is monoethyl trans-1,2-cyclopropanedicarboxylate, and the specific reaction formula is as follows:

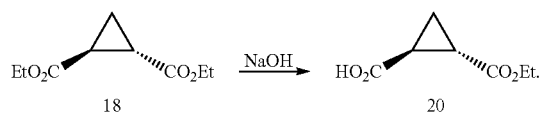

Step 2, 1 g, 6 mmol of Compound 20 was dissolved in 30 mL of dimethylformamide (DMF), then 4.6 g, 12 mmol of polypeptide condensing agent (HATU) and 3 mL of triethylamine were added into the above solution, then 0.6 g, 6 mmol of morpholine was added after stirring at room temperature for 0.5 h, and then stirred at room temperature overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; after drying by distillation, the above organic phase concentrated and dried by distillation was purified using column chromatography on silica gel, so as to obtain 1 g of colorless liquid with a yield of 77% as Compound 21; Compound 21 is ethyl (1s,2s)-2-morpholine-4-carbonyl) cyclopropanecarboxylate, and the specific reaction formula is as follows:

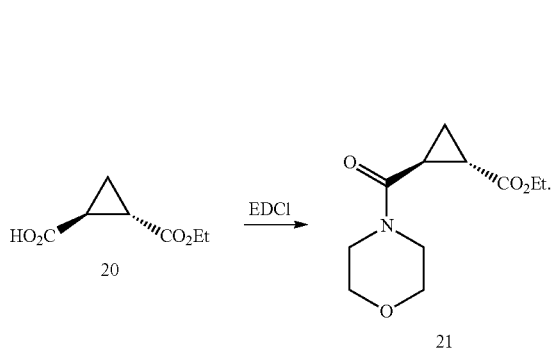 [SMILES: CCOC(=O)[C@H]1C[C@@H]1C(=O)O ; CCOC(=O)[C@H]1C[C@@H]1C(=O)N1CCOCC1]

Step 3, 1 g, 4 mmol of Compound 21 was dissolved in 30 mL of THF, 1N of 1 mol/L lithium aluminium hydride (LAH) solution was added under ice bath, and stirred at room temperature for 2 h; then the uniformly stirred reaction solution was filtered after quenching with sodium sulfate decahydrate; the organic phase obtained by extraction was washed with saturated saline solution and water, then anhydrous sodium sulfate was added for drying, and then concentrated and dried by distillation; purified by column chromatography on silica gel, and the above organic phase concentrated and dried by distillation was purified using column chromatography on silica gel, so as to obtain 0.5 g of colorless liquid as Compound 22 with a yield of 66%; Compound 22 is (1s,2s)-2-morpholine methyl) cyclopropyl methanol, and the specific reaction formula is as follows:

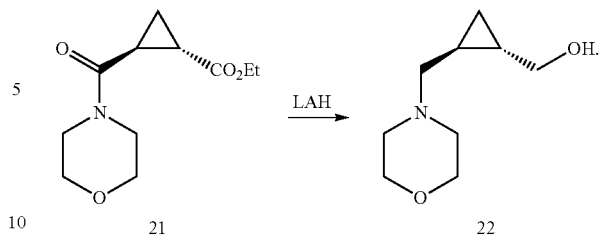

Step 4, 0.3 g, 1.7 mmol of Compound 22 was dissolved in 30 mL of dichloromethane, then 0.3 g, 3.4 mmol of N-methyl pyrrole and 0.3 g, 1.7 mmol of paratoluensulfonyl chloride were added into the above solution, and stirred at room temperature overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; the above organic phase concentrated and dried by distillation was purified using column chromatography on silica gel, so as to obtain 0.1 g of white solid with a yield of 18% as Compound 23; Compound 23 is methyl (1s,2s)-(2-morpholine methyl) cyclopropyl-p-methyl benzenesulfonate, and the specific reaction formula is as follows:

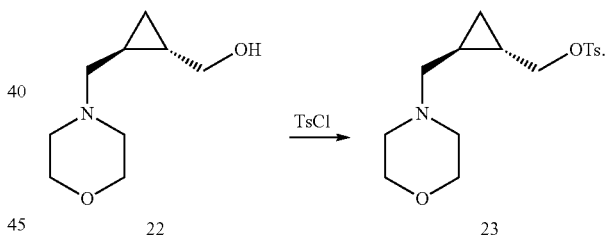

Step 5, 0.1 g, 0.2 mmol of compound A (compound A is N-p-fluorophenyl-N-3-fluoro-4-(6-methoxyl-7-hydroxyquinoline-4-) oxyphenyl cyclopropyl-1,1-dimethyl formamide) and 0.1 g, 0.3 mmol of Compound 23 were dissolved in 10 mL of acetonitrile, then 0.2 g, 0.5 mmol of cesium carbonate was added into the above solution, and stirred to reflux overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; after drying by distillation, the above organic phase concentrated and dried by distillation was purified using the reverse preparation method, so as to obtain 0.01 g of yellow solid with a yield of 8% as Compound 24; Compound 24 is N-p-fluorophenyl-N-3-fluoro-4-[6-methoxyl-7-(1S,2S)-2-morpholinomethyl cyclopropyl methoxyquinoline-4-] oxyphenyl cyclopropyl-1,1-dimethyl formamide, and the specific reaction formula is as follows:

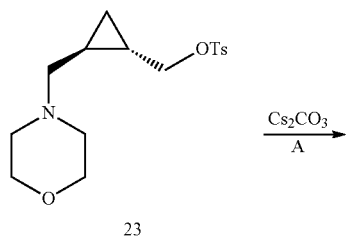

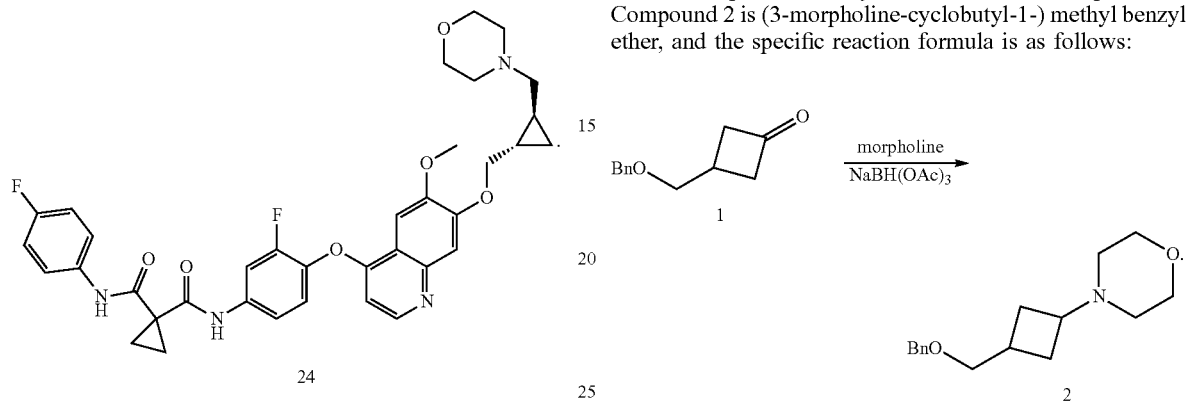

Example 2 Synthesis of Tyrosine Kinase Inhibitor Compound 5 and 1 drop of acetic acid were added into the above solution, and stirred to reflux overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; the above organic phase concentrated and dried by distillation was purified using column chromatography on silica gel, so as to obtain 1 g of colorless liquid with a yield of 73% as Compound 2; Compound 2 is (3-morpholine-cyclobutyl-1-) methyl benzyl ether, and the specific reaction formula is as follows:

Step 2, 1 g, 3.8 mmol of Compound 2 was dissolved into 30 mL of methalnol, then 0.1 g of palladium black and 2 mL of methanoic acid were added into the above solution, and

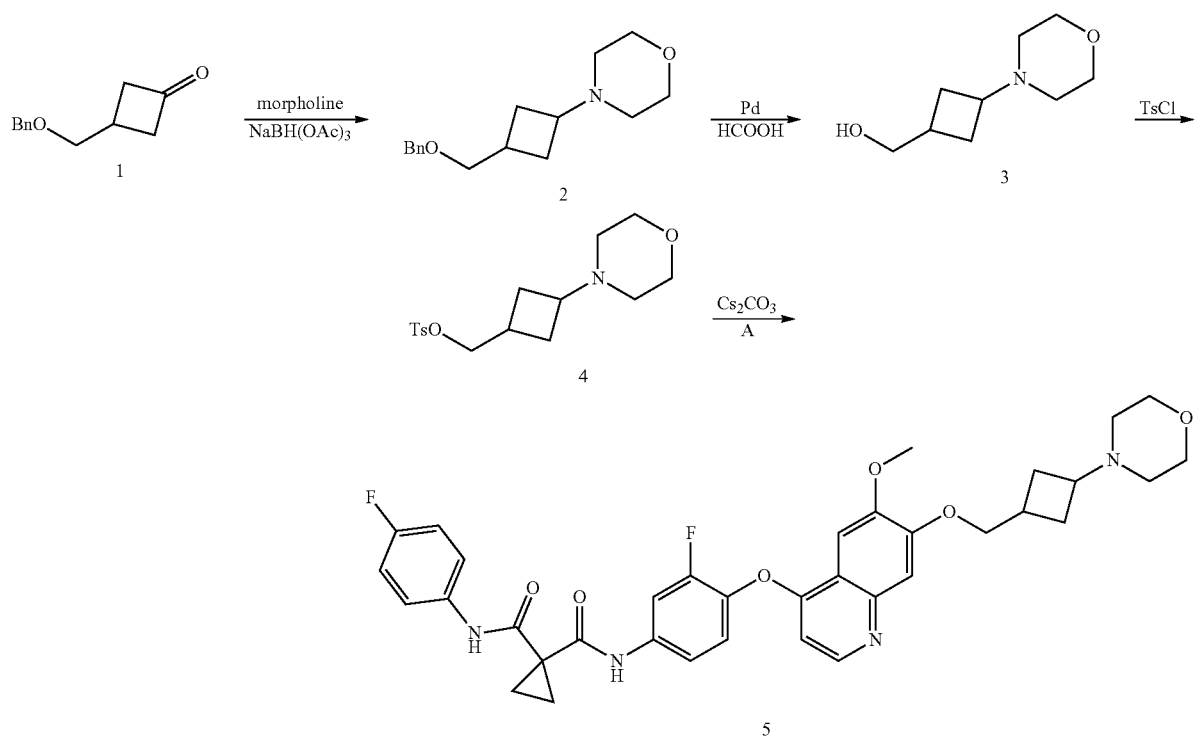

The method includes the following steps:

Step 1, 1 g, 5.2 mmol of Compound 1 (Compound 1 is 3-(benzyloxymethyl) cyclobutyl-1-ketone) and 0.46 g, 5.2 mmol of morpholine were dissolved in 30 mL of dichloroethane, then 3.3 g, 15.6 mmol of acetate sodium borohydride stirred to reflux overnight; the overnight reaction solution diluted with water, and then extracted with ethyl acetate; the organic phase obtained by extraction was washed with saturated saline solution and water, then anhydrous sodium sulfate was added for drying, and then concentrated and dried by distillation; the above organic phase concentrated and dried by distillation was purified using column chromatography on silica gel, so as to obtain 0.3 g of colorless liquid with a yield of 46% as Compound 3; Compound 3 is 3-morpholine-cyclobutyl methanol, and the specific reaction formula is as follows:

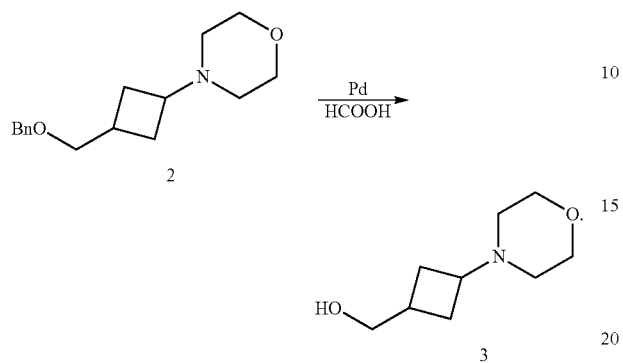

Step 3, 0.3 g, 1.7 mmol of Compound 3 was dissolved in 30 mL of dichloromethane, 0.3 g, 3.4 mmol of N-methyl pyrrole and 0.3 g, 1.7 mmol of paratoluensulfonyl chloride were added into the above solution, and stirred at room temperature overnight; the overnight reaction solution was diluted with water, and then extracted with ethyl acetate; the organic phase obtained by extraction was washed with saturated saline solution and water, anhydrous sodium sulfate was added for drying, and then concentrated and dried by distillation; the above organic phase concentrated and dried by distillation was purified using column chromatography on silica gel, so as to obtain 0.2 g of white solid with a yield of 35% as Compound 4; Compound 4 is N-p-fluorophenyl-N-3-fluoro-4-(6-methoxy-7-hydroxyquinoline-4-) oxyphenyl cyclopropyl-1,1-dimethyl formamide, and the specific reaction formula is as follows:

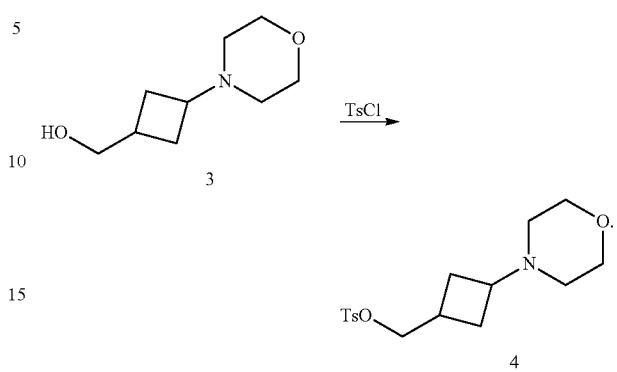

Step 4, 0.1 g, 0.2 mmol of compound A (compound A is N-p-fluorophenyl-N-3-fluoro-4-(6-methoxyl-7-hydroxyquinoline-4-) oxyphenyl cyclopropyl-1,1-dimethyl formamide) and 0.1 g, 0.3 mmol of Compound 4 were dissolved in 10 mL of acetonitrile, 0.2 g, 0.5 mmol of cesium carbonate was added, and stirred to reflux overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; after drying by distillation, the above organic phase concentrated and dried by distillation was purified using the reverse preparation method, so as to obtain 0.02 g of yellow solid with a yield of 16% as Compound 5; Compound 5 is N-p-fluorophenyl-N-3-fluoro-4-[6-methoxyl-7-(3-morpholine-cyclobutyl) methoxyquinoline-4-] oxyphenyl cyclopropyl-1,1-dimethyl formamide), and the specific reaction formula is as follows:

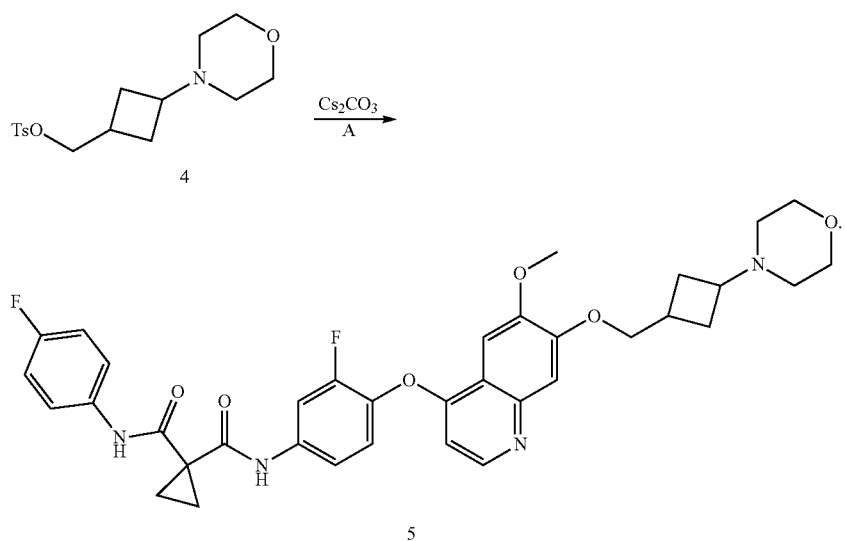

Example 3 Synthesis of Tyrosine Kinase Inhibitor Compound 10

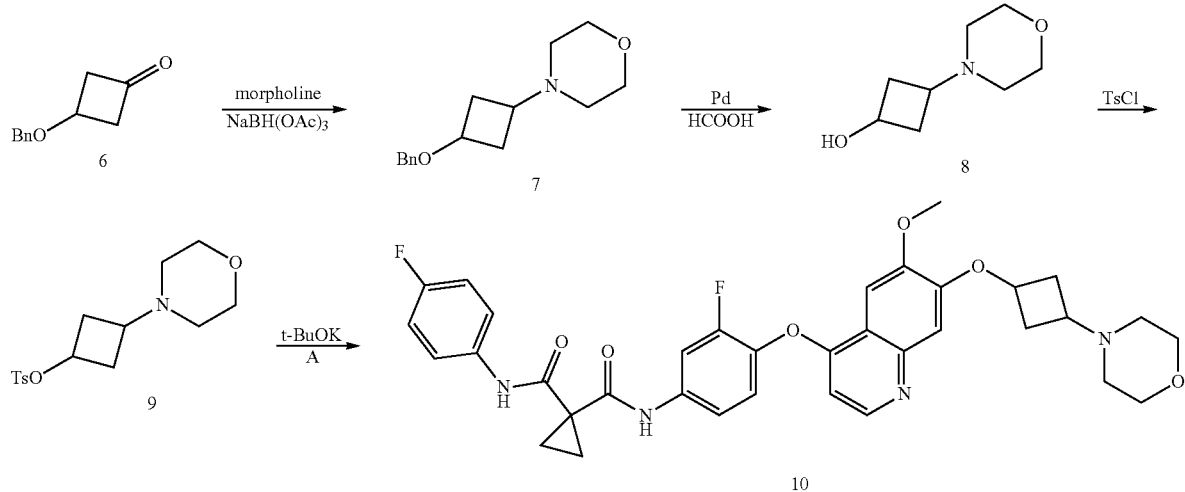

The method includes the following steps:

Step 1, 1 g, 5.2 mmol of Compound 6 (Compound 6 is 3-benzyloxy cyclobutyl-1-ketone) and 0.46 g, 5.2 mmol of morpholine were dissolved in 30 mL of dichloroethane, 3.3 g, 15.6 mmol of acetate sodium borohydride and 1 drop of acetic acid were added into the above solution, and stirred at room temperature overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; the above organic phase concentrated and dried by distillation was purified using column chromatography on silica gel, so as to obtain 1.1 g of colorless liquid with a yield of 80% as Compound 7; Compound 7 is 3-morpholine-cyclobutyl benzyl ether, and the specific reaction formula is as follows:

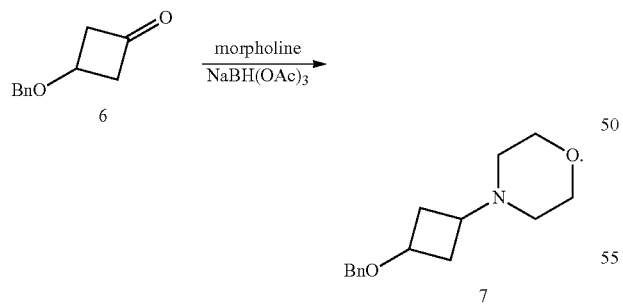

Step 2, 1 g, 3.8 mmol of Compound 7 was dissolved in 30 mL of methalnol, 0.1 g of palladium black and 2 mL of methanoic acid were added into the above solution, and stirred to reflux overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; the above organic phase concentrated and dried by distillation was purified using column chromatography on silica gel, so as to obtain 0.3 g of colorless liquid with a yield of 46% as Compound 8; Compound 8 is 3-morpholine-cyclobutanol, and the specific reaction formula is as follows:

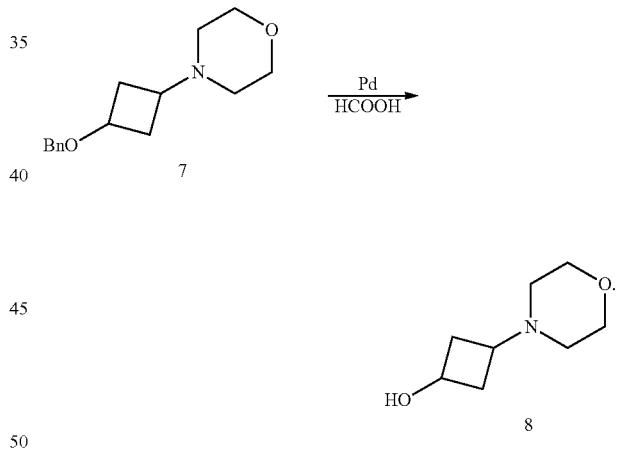

Step 3, 0.3 g, 1.7 mmol of Compound 8 was dissolved in 30 mL of dichloromethane, 0.3 g, 3.4 mmol of N-methyl pyrrole and 0.3 g, 1.7 mmol of paratoluensulfonyl chloride was added into the above solution, and stirred at room temperature overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; the above organic phase concentrated and dried by distillation was purified using column chromatography on silica gel, so as to obtain 0.1 g of white solid with a yield of 18% as Compound 9; Compound 9 is p-toluenesulfonic acid (3-morpholine-cyclobutyl) ether, and the specific reaction formula is as follows:

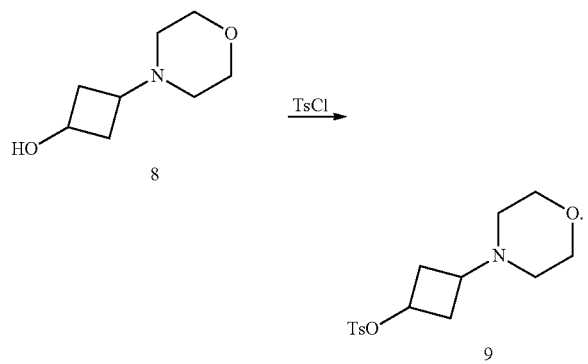

Step 4, 0.1 g, 0.2 mmol of Compound A was dissolved in 10 mL of dioxane, compound A is N-p-fluorophenyl-N-3-fluoro-4-(6-methoxyl-7-hydroxyquinoline-4-) oxyphenyl cyclopropyl-1,1-dimethyl formamide, 0.02 g, 0.2 mmol of potassium tert-butoxide was added into the above solution, 0.1 g, 0.3 mmol of Compound 9 was added after stirring at room temperature for 0.5 h, and then stirred at 50° C. overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; after drying by distillation, the above organic phase concentrated and dried by distillation was purified using the reverse preparation method, so as to obtain 0.1 g of yellow solid with a yield of 8% as Compound 10; Compound 10 is N-p-fluorophenyl-N-3-fluoro-4-[6-methoxyl-7-(3-morpholine-cyclobutyl) oxyquinoline-4-] oxyphenyl cyclopropyl-1,1-dimethyl formamide, and the specific reaction formula is as follows:

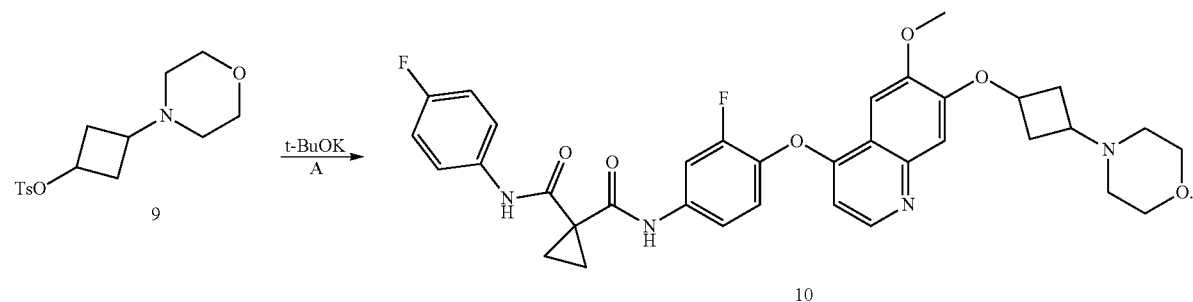

Example 4 Synthesis of Tyrosine Kinase Inhibitor Compound 38

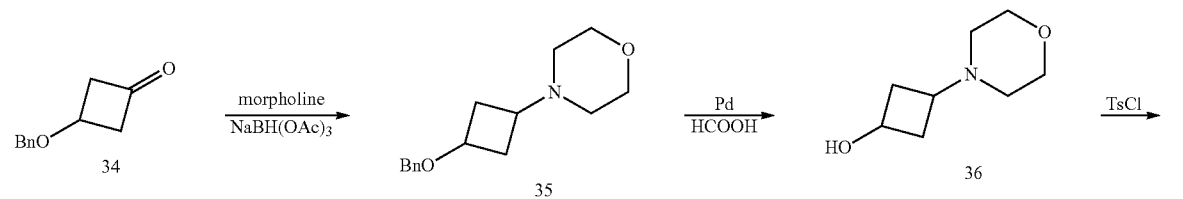

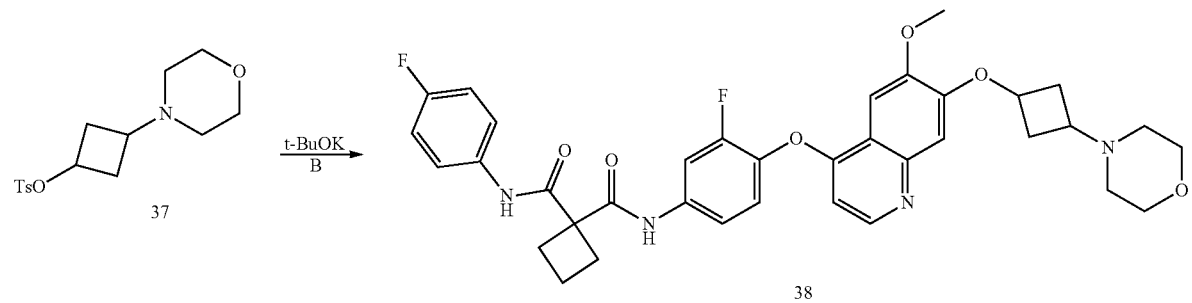

Compound B has the structural formula below:

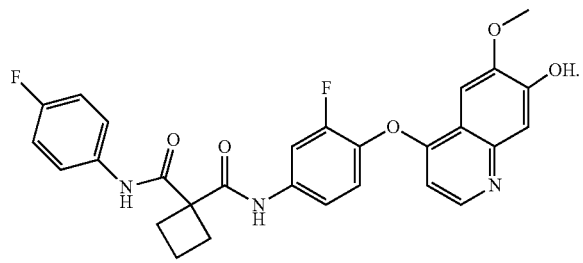 [SMILES: COc1cc2c(Oc3ccc(NC(=O)C4(C(=O)Nc5ccc(F)cc5)CCC4)cc3F)ccnc2cc1O]

The method includes the following steps:

Step 1, 1 g, 5.2 mmol of Compound 34 and 0.46 g, 5.2 mmol of morpholine were dissolved in 30 mL of dichloroethane, Compound 34 is 3-benzyloxy cyclobutyl-1-ketone, 3.3 g, 15.6 mmol of acetate sodium borohydride and 1 drop of acetic acid were add into the above solution, and stirred at room temperature overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; the above organic phase concentrated and dried by distillation was purified using column chromatography on silica gel, so as to obtain 1.1 g of colorless liquid with a yield of 80% as Compound 35; Compound 35 is 3-morpholine-cyclobutyl benzyl ether, and the specific reaction formula is as follows:

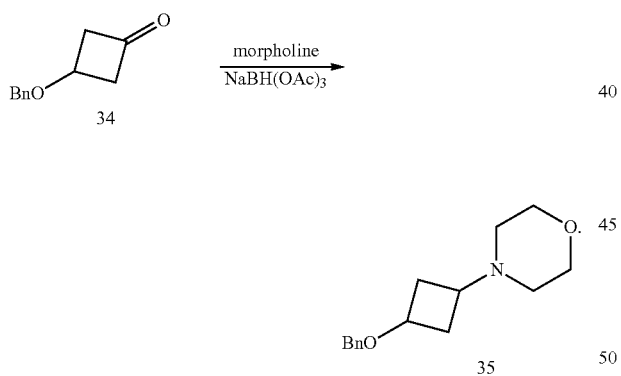

Step 2, 1 g, 3.8 mmol of Compound 35 was dissolved in 30 mL of methanol, 0.1 g of palladium black and 2 mL of methanoic acid were added into the above solution, and stirred to reflux overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; the above organic phase concentrated and dried by distillation was purified using column chromatography on silica gel, so as to obtain 0.3 g of colorless liquid with a yield of 46% as Compound 36; Compound 36 is 3-morpholine-cyclobutanol, and the specific reaction formula is as follows:

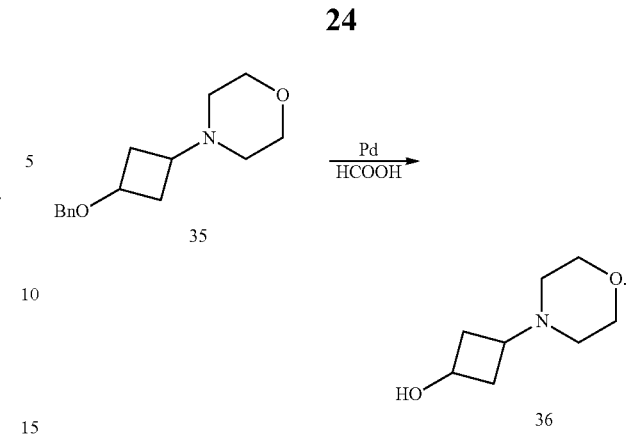

Step 3, 0.3 g, 1.7 mmol of Compound 36 was dissolved in 30 mL of dichloromethane, 0.3 g, 3.4 mmol of N-methyl pyrrole and 0.3 g, 1.7 mmol of paratoluensulfonyl chloride were added, and stirred at room temperature overnight; the overnight reaction solution was diluted with water, and then extracted with ethyl acetate; the organic phase obtained by extraction was washed with saturated saline solution and water, then anhydrous sodium sulfate was washed for drying, and then concentrated and dried by distillation; the above organic phase concentrated and dried by distillation was purified using column chromatography on silica gel, so as to obtain 0.1 g of white solid with a yield of 18% as Compound 37; Compound 37 is 3-morpholine-cyclobutyl benzyl ether, and the specific reaction formula is as follows:

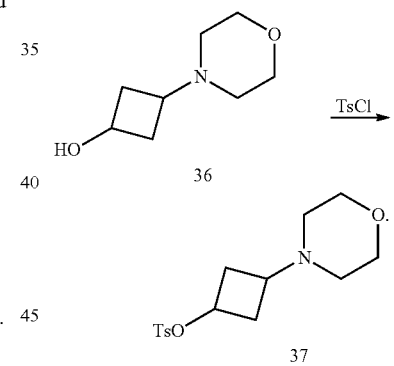

Step 4, 0.1 g, 0.2 mmol of Compound B was dissolved in 10 mL of dioxane, compound B is N-p-fluorophenyl-N-3-fluoro-4-(6-methoxyl-7-hydroxyquinoline-4-) oxyphenyl cyclobutyl-1,1-dimethyl formamide, 0.02 g, 0.2 mmol of potassium tert-butoxide was add, 0.1 g, 0.3 mmol of Compound 33 was added after stirring at room temperature for 0.5 h, Compound 33 is p-tuluenesulfonic acid (3-morpholine-cyclobutyl) ester, and then stirred at 50° C. overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; after drying by distillation, the above organic phase concentrated and dried by distillation was purified using the reverse preparation method, so as to obtain 0.01 g of yellow solid with a yield of 8% as Compound 38; Compound 38 is N-p-fluorophenyl-N-3-fluoro-4-[6-methoxyl-7-(3-morpholinecyclobutyl) oxyquinoline-4-] oxyphenyl cyclobutyl-1,1-dimethyl formamide, and the specific reaction formula is as follows:

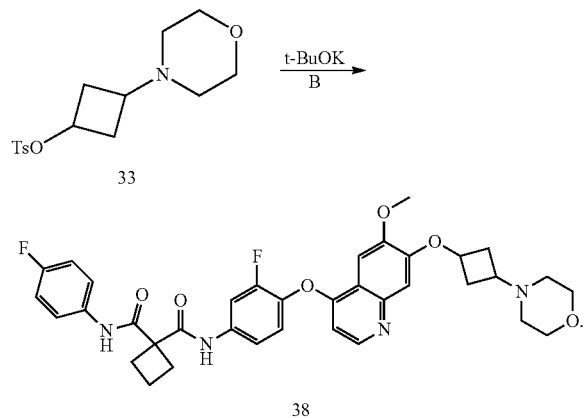

Example 5 Synthesis of Tyrosine Kinase Inhibitor Compound 15

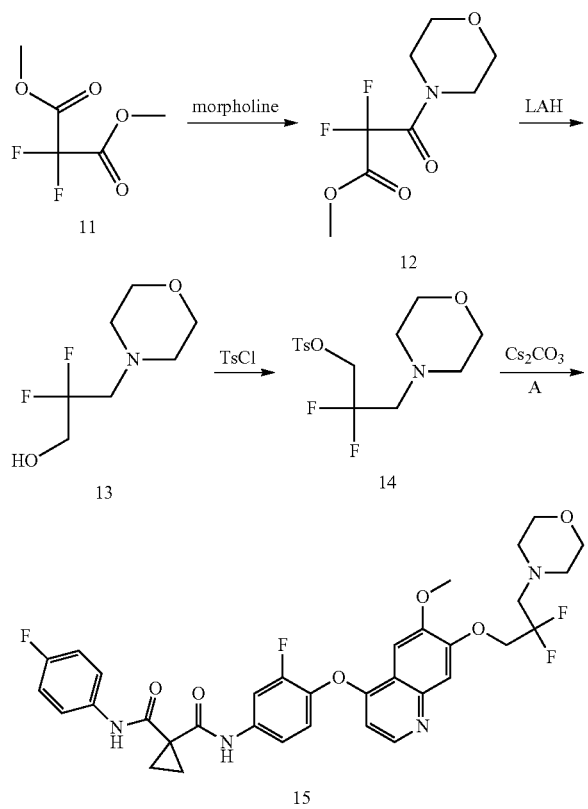

The method includes the following steps:

Step 1, 2 g, 12 mmol of Compound 11 and 1 g, 12 mmol of morpholine were dissolved in 30 mL of DMF, Compound 11 is dimethyl 2,2-difluoromalonate, and stirred at 100° C. overnight; the overnight reaction solution was diluted with water, and then extracted with ethyl acetate; the organic phase obtained by extraction was washed with saturated saline solution and water, then anhydrous sodium sulfate was added for drying, and then concentrated and dried it by distillation; the above organic phase concentrated and dried by distillation was purified using column chromatography on silica gel, so as to obtain 1.5 g of colorless liquid with a yield of 57% as Compound 12; Compound 12 is methyl 2,2-difluoro-3-morpholine-3-oxopropionate, and the specific reaction formula is as follows:

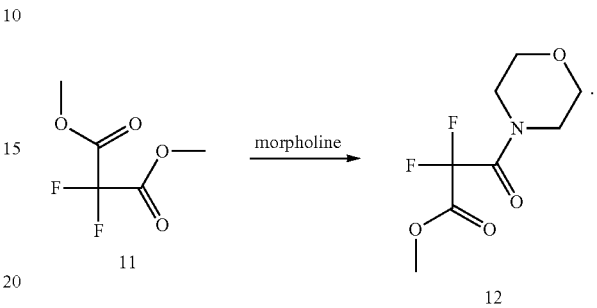

Step 2, 1.5 g, 7 mmol of Compound 12 was dissolved in 30 mL of tetrahydronfuran (THF), 1 mol/L of 28 mL, 28 mmol LAH was added under ice bath, and stirred at room temperature for 2 h; then the overnight reaction solution was filtered after quenching with sodium sulfate decahydrate; the organic phase obtained by extraction was washed with saturated saline solution and water, then anhydrous sodium sulfate was added for drying, and then concentrated and dried by distillation; the above organic phase concentrated and dried by distillation was purified using column chromatography on silica gel, so as to obtain 0.5 g of colorless liquid with a yield of 41% as Compound 13; Compound 13 is 2,2-difluoro-3-morpholine-1-propyl alcohol, and the specific reaction formula is as follows:

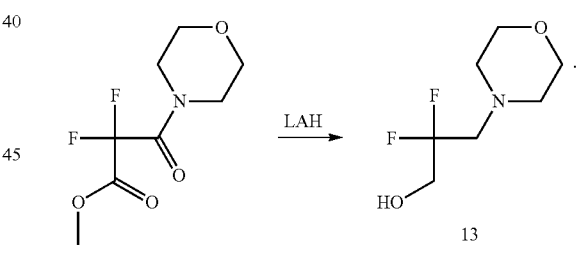

Step 3, 0.3 g, 1.7 mmol of Compound 13 was dissolved in 30 mL of dichloromethane, 0.3 g, 3.4 mmol of N-methyl pyrrole and 0.3 g, 1.7 mmol of paratoluensulfonyl chloride were added into the above solution, and stirred at room temperature overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; the above organic phase concentrated and dried by distillation was purified using column chromatography on silica gel, so as to obtain 0.1 g of white solid with a yield of 18% as Compound 14; Compound 14 is (2,2-difluoro-3-morpholine-1-) propyl p-tuluenesulfonate, and the specific reaction formula is as follows:

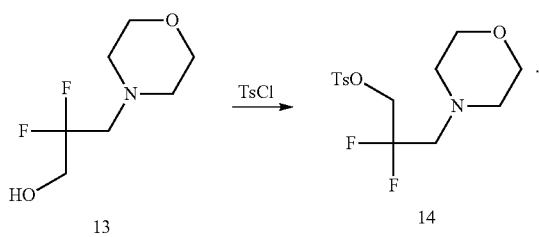

line-4-]oxyphenyl cyclopropyl-1,1-dimethyl formamide, and the specific reaction formula is as follows:

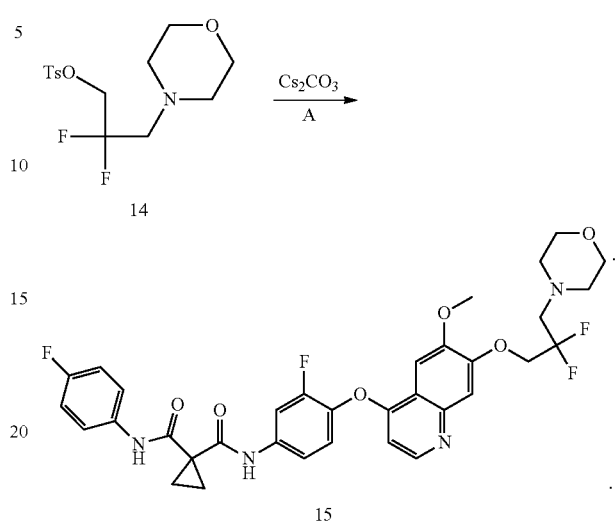

Step 4, 0.1 g, 0.2 mmol of Compound A and 0.1 g, 0.3 mmol of Compound 14 were dissolved in 10 mL of acetonitrile, compound A is N-p-fluorophenyl-N-3-fluoro-4-(6-methoxyl-7-hydroxyquinoline-4-) oxyphenyl cyclopropyl-1,1-dimethyl formamide, 0.2 g, 0.5 mmol of cesium carbonate was added into the above solution, and stirred to reflux overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; after drying by distillation, the above organic phase concentrated and dried by distillation was purified using the reverse preparation method, so as to obtain 0.01 g of yellow solid with a yield of 8% as Compound 15; Compound 15 is N-p-fluorophenyl-N-3-fluoro-4-[6-methoxyl-7-(2,2-difluoro-3-morpholine-1-) propoxy quino- Example 6 Synthesis of Tyrosine Kinase Inhibitor Compound 27 compound A is

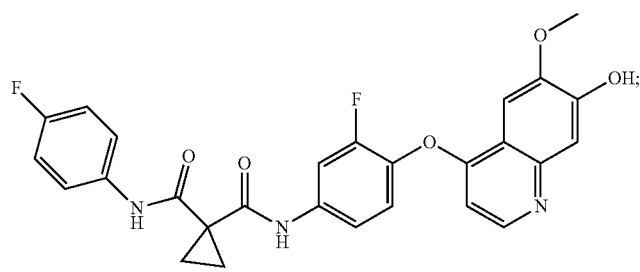

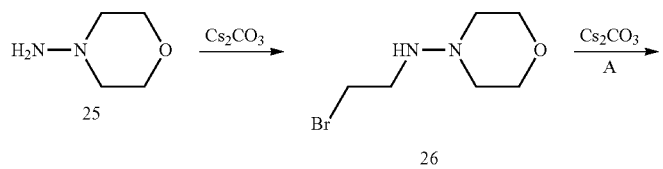

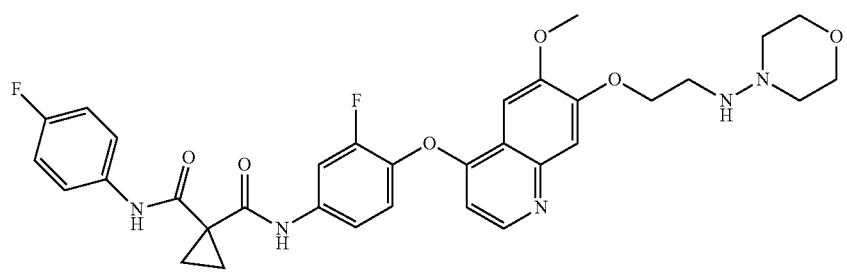

The method includes the following steps:

Step 1, 0.1 g, 1 mmol of Compound 25 and 0.18 g, 1 mmol of 1,2-dibromoethane were dissolved in 10 mL of acetonitrile, Compound 25 is N-aminomorpholine, 0.65 g, 2 mmol of cesium carbonate was added into the above solution, and stirred at room temperature overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; after drying by distillation, the above organic phase concentrated and dried by distillation was purified using column chromatography on silica gel, so as to obtain 0.1 g of colorless liquid with a yield of 50% as Compound 26; Compound 26 is N-(2-bromomethyl) morpholine-4-amine, and the specific reaction formula is as follows:

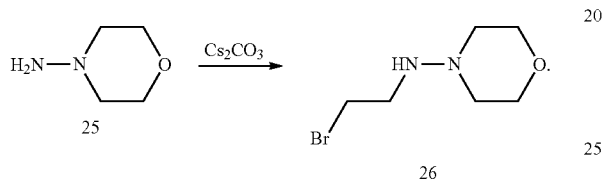

Step 2, 0.1 g, 0.2 mmol of Compound A and 0.06 g, 0.3 mmol of Compound 26 were dissolved in mL of acetonitrile, compound A is N-p-fluorophenyl-N-3-fluoro-4-(6-methoxyl-7-hydroxyquinoline-4-) oxyphenyl cyclopropyl-1,1-dimethyl formamide, 0.2 g, 0.5 mmol of cesium carbonate was added into the above solution, and stirred to reflux overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; after drying by distillation, the above organic phase concentrated and dried by distillation was purified using the reverse preparation method, so as to obtain 0.01 g of yellow solid with a yield of 8% as Compound 27; Compound 27 is N-p-fluorophenyl-N-3-fluoro-4-[6-methoxyl-7-(morpholine-4-amine) ethoxyquinoline-4-]oxyphenyl cyclopropyl-1,1-dimethyl formamide, and the specific reaction formula is as follows:

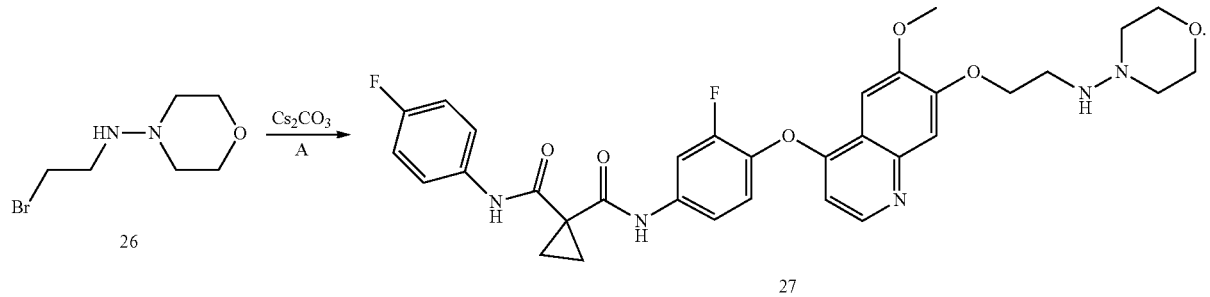

Example 7 Synthesis of Tyrosine Kinase Inhibitor Compound 30

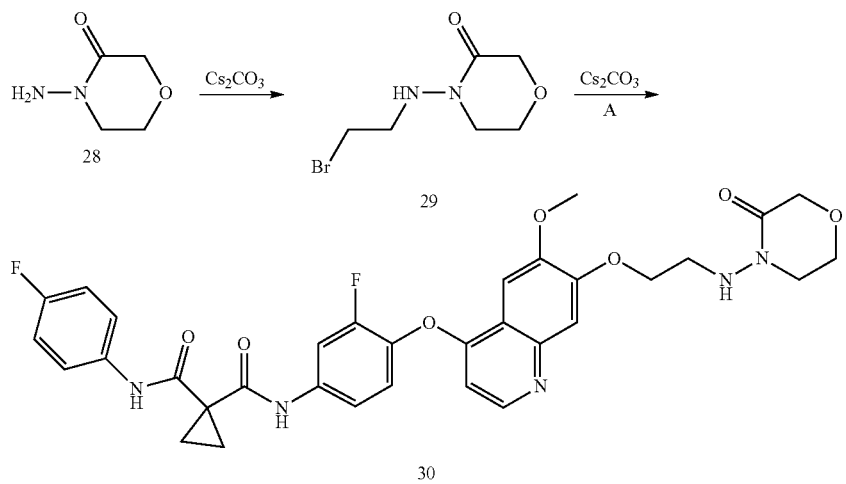

The method includes the following steps:

Step 1, 0.1 g, 1 mmol of Compound 28 and 0.18 g, 1 mmol of 1,2-dibromoethane were dissolved in 10 mL of acetonitrile, Compound 28 is 4-aminoquinoline-3-ketone, 0.65 g, 2 mmol of cesium carbonate was added into the above solution, and stirred at room temperature overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; after drying by distillation, the above organic phase concentrated and dried by distillation was purified using column chromatography on silica gel, so as to obtain 0.1 g of colorless liquid with a yield of 50% as Compound 29; Compound 29 is (2-bromoethylamine) morpholine-3-ketone, and the specific reaction formula is as follows:

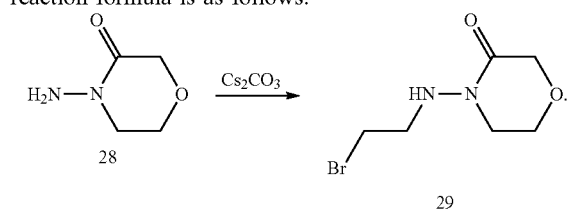

Step 2, 0.1 g, 0.2 mmol of Compound A and 0.06 g, 0.3 mmol of Compound 29 were dissolved in 10 mL of acetonitrile, compound A is N-p-fluorophenyl-N-3-fluoro-4-(6-methoxyl-7-hydroxyquinoline-4-) oxyphenyl cyclopropyl-1,1-dimethyl formamide, 0.2 g, 0.5 mmol of cesium carbonate was added into the above solution, and stirred to reflux overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; after drying by distillation, the above organic phase concentrated and dried by distillation was purified using the reverse preparation method, so as to obtain 0.012 g of yellow solid with a yield of 9% as Compound 30, Compound 30 is N-p-fluorophenyl-N-3-fluoro-4-[6-methoxyl-7-(3-oxomorpholine amine) ethoxyquinoline-4-] oxyphenyl cyclopropyl-1,1-dimethyl formamide, and the specific reaction formula is as follows:

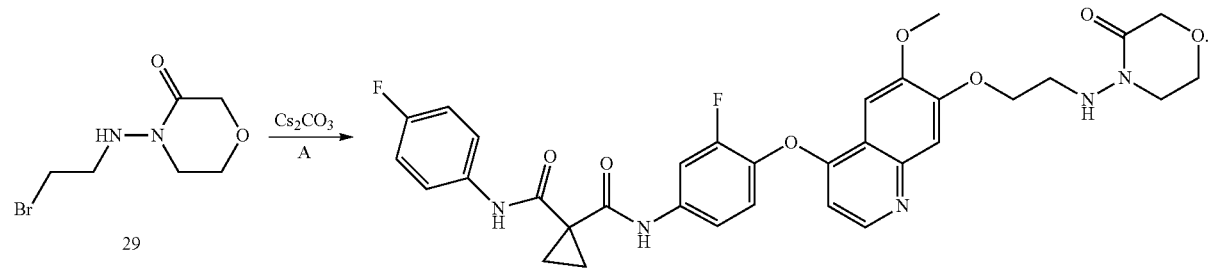

Example 8 Synthesis of Tyrosine Kinase Inhibitor Compound 33

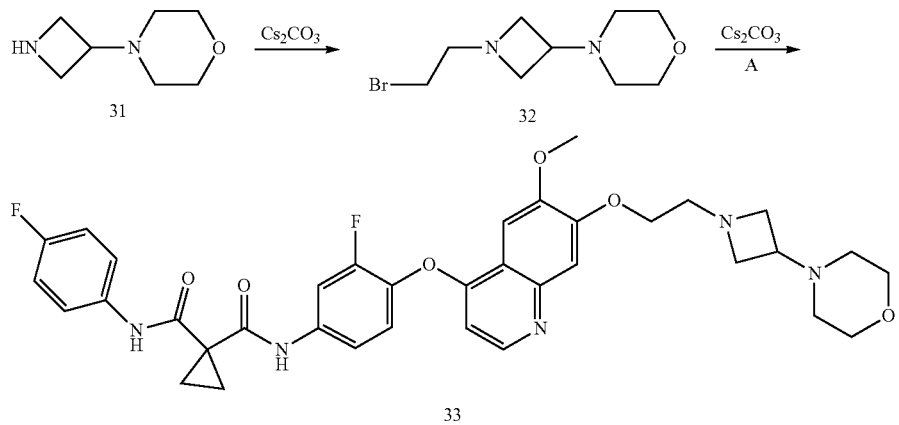

The method includes the following steps:

Step 1, 0.1 g, 0.7 mmol of Compound 31 and 0.12 g, 0.7 mmol of 1,2-dibromoethane were dissolved in 10 mL of acetonitrile, Compound 31 is 3-morpholine azetidine, 0.65 g, 2 mmol of cesium carbonate was added into the above solution, and stirred at room temperature overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; the above organic phase concentrated and dried by distillation was purified using column chromatography on silica gel, so as to obtain 0.1 g of colorless liquid with a yield of 50% as compound 32; Compound 32 is bromoethylazetidine morpholine, and the specific reaction formula is as follows:

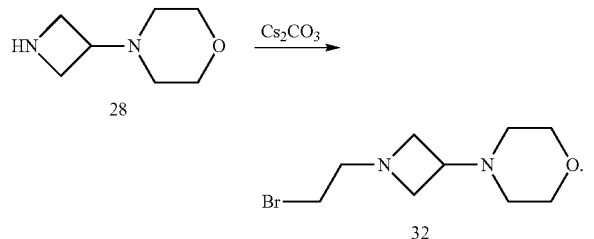

Step 2, 0.1 g, 0.2 mmol of Compound A and 0.06 g, 0.24 mmol of Compound 32 were dissolved in 10 mL of acetonitrile, compound A is N-p-fluorophenyl-N-3-fluoro-4-(6-methoxyl-7-hydroxyquinoline-4-) oxyphenyl cyclopropyl-1,1-dimethyl formamide, 0.2 g, 0.5 mmol of cesium carbonate was added into the above solution, and stirred to reflux overnight; the overnight reaction solution was diluted with water, and then extracted with ethyl acetate; the organic phase obtained by extraction was washed with saturated saline solution and water, then anhydrous sodium sulfate was added for drying, and then concentrated and dried by distillation; after drying by distillation, the above organic phase concentrated and dried was purified by distillation using the reverse preparation method, so as to obtain 0.09 g of yellow solid with a yield of 8% as Compound 33; Compound 33 is N-p-fluorophenyl-N-3-fluoro-4-[6-methoxyl-7-(morpholine-3-azetidine-1-)ethoxyquinoline-4-]oxyphenyl cyclopropyl-1, 1-dimethyl formamide, and the specific reaction formula is as follows:

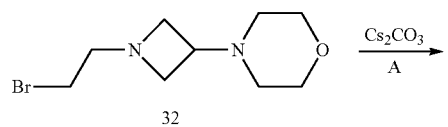

-continued

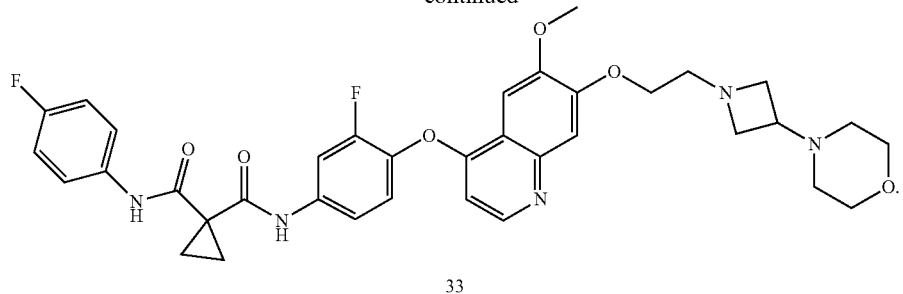

33

Example 9 Detection of the Inhibitory Activities of Tyrosine Kinases

The compounds in the above Examples are used for detecting and screening the inhibitory activities of C-MET and KDR kinase.

1. Methods (1) 4 μL of prepared kinase buffer solution or 4 μL of kinase solution (100% inhibition control) were added into a 384-hole plate; 2 μL of the compound or 2 μL of buffer without the compound (0% inhibition control) was added into the holes; 2 repetitive holes were set for all the samples or control above.

(2) Incubated at 25° C. for 5 min;

(3) 2 μL of ATP/substrate/$MgCl_2$/$MnCl_2$/SEB/DTT mixed solution were added into the holes;

(4) Centrifugated at 1000 rpm for 1 min, and incubated by vibration at 30° C. for 30 min;

(5) 8 μL of XL-665/antibody mixed solution were added into the holes;

(6) Incubated at 25° C. for 1 h;

(7) The signals at 665 nm and 620 nm were read on PHERAstar FS;

(8) The data was analyzed according to the instructions of the kit, and the fitting calculation of IC50 was performed using GraphPad Prism5.

Ratio=665 nm/620 nm $$\text{Inhibition rate of samples }\% = \left(\frac{Ratio_{sample} - Ratio_{negative}}{Ratio_{positive} - Ratio_{negative}}\right) \times 100$$

2. Experimental Results

The detection results of the detected compounds and reference compound are summarized as shown in the following Table 1 and Table 2, wherein, the control compound is the existing C-MET kinase inhibitor Foretinib (with the structural formula below). The chemical structural formula of For-Oxide and For-Methyl are as below, respectively.

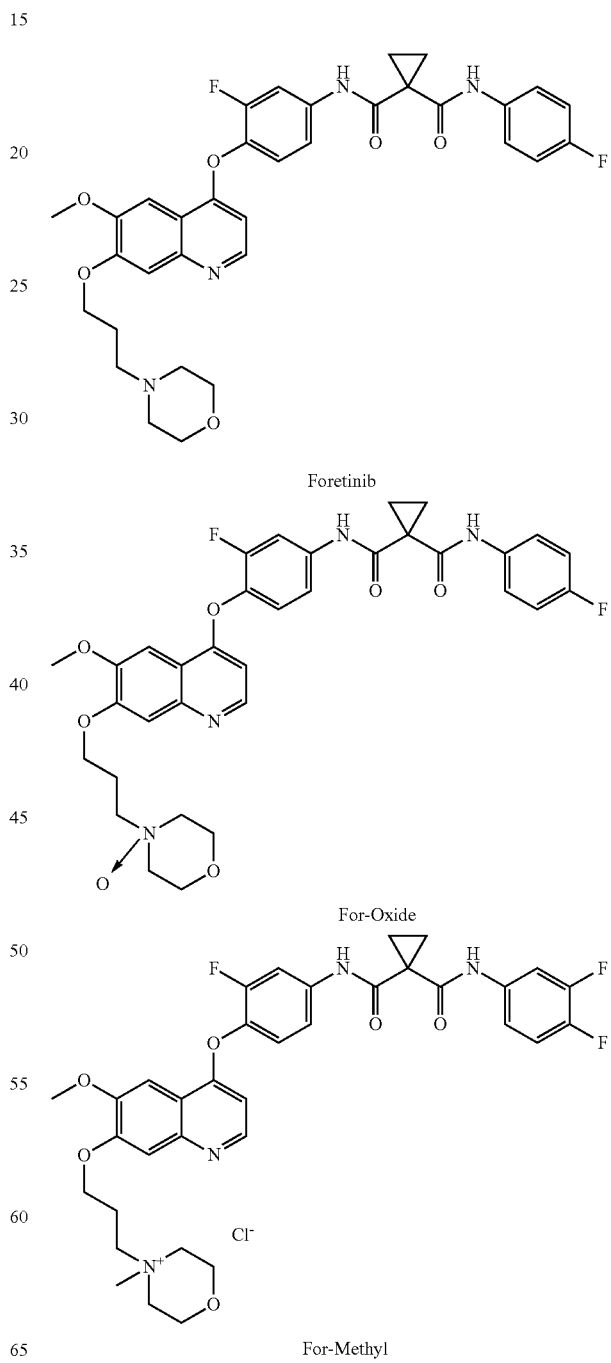

TABLE 1

Inhibitory activities of the Compounds on C-MET

| Compound No. | cMet IC50 (nM) | IC50 95 Confidence Interval (nM) | Curve $R^2$ |
|---|---|---|---|
| Foretinib | 7.491 | 5.829 to 9.627 | 0.9884 |
| For-Oxide | 2.911 | 2.204 to 3.844 | 0.9850 |
| For-Methyl | 162.7 | 107.8 to 245.5 | 0.9697 |
| Compound 10 | 17.04 | 12.35 to 23.51 | 0.9814 |
| Compound 5 | 20.55 | 17.07 to 24.74 | 0.9815 |
| Compound 15 | 6.641 | 4.713 to 8.552 | 0.9672 |
| Compound 24 | 25.21 | 20.21 to 29.92 | 0.9770 |
| Compound 33 | 15.01 | 11.23 to 18.58 | 0.9711 |
| Reference Compound SCR-1510 (experimental internal reference) | 2.751 | 1.841 to 4.139 | 0.9685 |

TABLE 2

Inhibitory activities of the Compounds on KDR

| Compound No. | KDR IC50 (nM) | IC50 95 Confidence Interval (nM) | Curve $R^2$ |
|---|---|---|---|
| Foretinib | 14.83 | 11.33 to 19.41 | 0.9741 |
| For-Oxide | 10.6 | 8.628 to 13.09 | 0.9836 |
| Compound 10 | 64.16 | 54.00 to 76.24 | 0.9881 |
| Compound 5 | 39.93 | 32.27 to 49.41 | 0.9714 |
| Positive Ref | 6774 | 5424 to 8460 | 0.8963 |

It can be known from the data of Tables 1-2 that the compounds in the above embodiments of the invention have inhibitory activities on the tyrosine kinases of C-MET, KDR, etc.

Example 10 Test of Inhibition on the Proliferation of Tumor Cells

1. Methods (1) Culture cells: The tumor cells (such as human lung adenocarcinoma cells HCC78, human malignant glioma cells U87MG, human gastric cancer cells MKN-45, human umbilical vein endothelial cells HUVEC, human lung adenocarcinoma cells A549, etc.) were cultured in culture medium; culture conditions: 37° C., 5% $CO_2$.

(2) Inoculate cells: The cells at the exponential growth phase and in good state were taken, and an appropriate amount of pancreatin for cell dissociation was added thereto, the cells were collected for centrifugation, and the supernatant was discarded. The cells were resuspended with the culture solution containing serum, then counted, and the cell suspensions were taken and inoculated in a 96-hole plate at 3000/hole, 90 μL/hole. The culture plate was transferred into a constant temperature $CO_2$ incubator, and cultured under the conditions of 37° C., 5% $CO_2$ and saturated humidity for 24 h.

(3) Add the test compounds: 10 μL/hole, culture for 72 h, 3 parallel holes were set for each group.

(4) Determine the results: After 72 h of action for the compounds, 10 μL/hole CCK8 was added, incubated in the incubator for an appropriate time, and the absorbance was measured at 450 nm.

2. Experimental Results

The detection results of the detected compounds are summarized as shown in Tables 3-6:

TABLE 3

Results of Inhibition on the Proliferation of Human Lung Adenocarcinoma Cells HCC78 (see FIG. 1 for the corresponding fitted curve)

| Compound No. | HCC78 IC50 (μM) | 95% Confidence Interval (μM) |
|---|---|---|
| Foretinib | 0.1886 | 0.1253 to 0.2839 |
| For-Oxide | 0.1182 | 0.06890 to 0.2030 |
| For-Methyl | >10 | / |
| Compound 10 | 0.1072 | 0.06939 to 0.1656 |
| SCR-1510 | 1.779 | 1.001 to 3.160 |

TABLE 4

Figure 2:
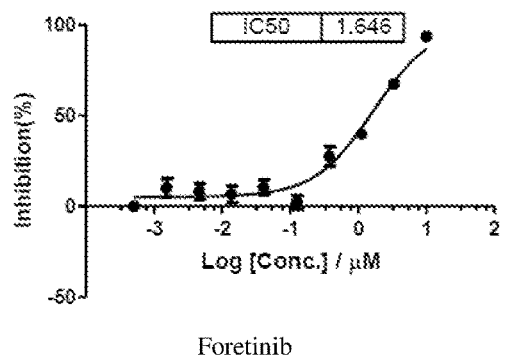
FIG. 2 is the fitted curve for the inhabitation on the proliferation of human malignant glioma cells U87MG in Example 10 of the invention.
Figure 2:
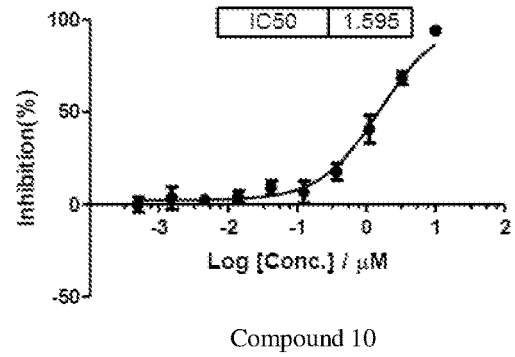
Figure 2:
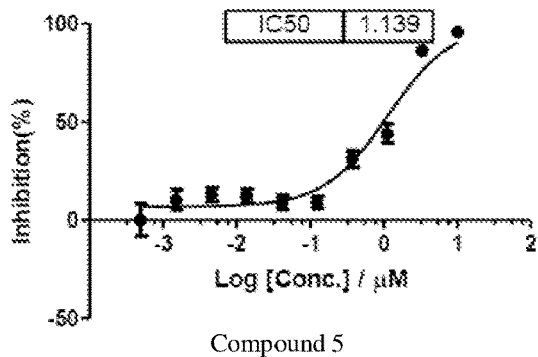
Figure 3:
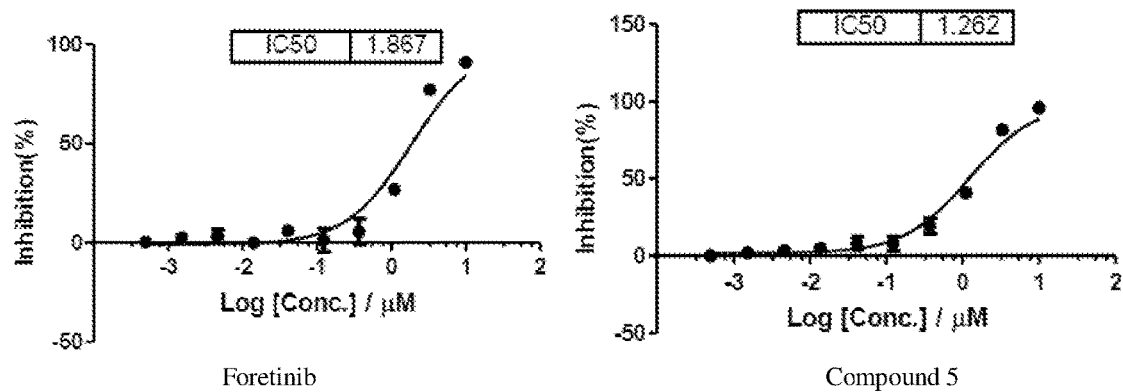
FIG. 3 is the fitted curve for the inhabitation on the proliferation of human gastric cancer cells MKN-45 in Example 10 of the invention.
Figure 4:
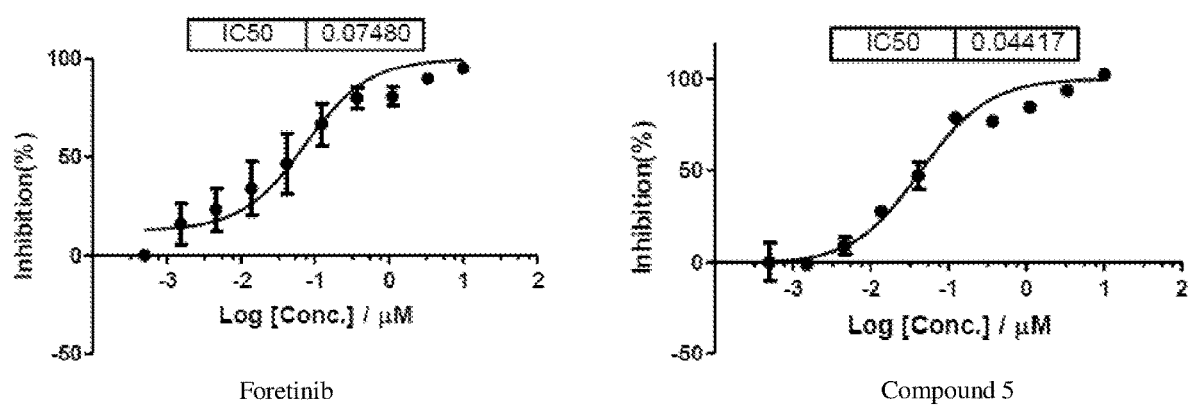
FIG. 4 is the fitted curve for the inhabitation on the proliferation of human lung adenocarcinoma cells HCC78 in Example 10 of the invention.

Results of Inhibition on the Proliferation of Human Malignant Glioma Cells U87MG Human Gastric Cancer Cells MKN-45 and Human Lung Adenocarcinoma Cells HCC78 (see FIG. 2~FIG. 4 for the corresponding fitted curves)

| | U87MG | | | MKN-45 | | |
|---|---|---|---|---|---|---|
| Compound No. | IC50 (μM) | 95% Confidence Interval (μM) | $R^2$ | IC50 (μM) | 95% Confidence Interval (μM) | $R^2$ |
| Foretinib | 1.646 | 1.255 to 2.160 | 0.9424 | 1.867 | 1.387 to 2.513 | 0.9328 |
| Compound 10 | 1.595 | 1.226 to 2.074 | 0.9473 | 3.205 | 2.788 to 3.684 | 0.9751 |
| Compound 5 | 1.139 | 0.8225 to 1.576 | 0.9323 | 1.262 | 0.9934 to 1.602 | 0.9613 |

TABLE 4-continued

Results of Inhibition on the Proliferation of Human Malignant Glioma Cells U87MG Human Gastric Cancer Cells MKN-45 and Human Lung Adenocarcinoma Cells HCC78 (see FIG. 2~FIG. 4 for the corresponding fitted curves)

| | HCC78 | | |
|---|---|---|---|
| | IC50 (μM) | 95% Confidence Interval (μM) | $R^2$ |
| Foretinib | 0.07480 | 0.03897 to 0.1435 | 0.8136 |
| Compound 10 | / | / | / |
| Compound 5 | 0.04417 | 0.03120 to 0.06254 | 0.9471 |

TABLE 5

Figure 5:
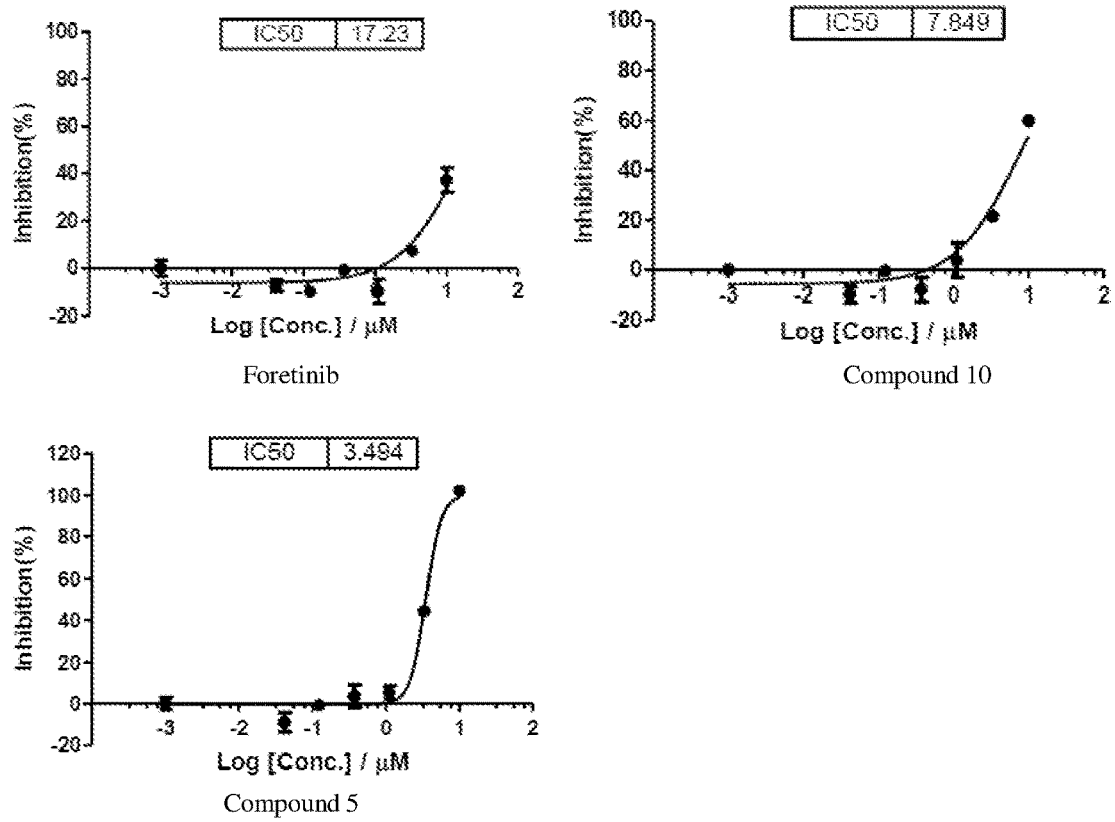
FIG. 5 is the fitted curve for the inhabitation on the proliferation of human ovarian cancer cells SK-OV-3 in Example 10 of the invention.

Results of Inhibition on the Proliferation of Human Ovarian Cancer Cells SK-OV-3 (see FIG. 5 for the corresponding fitted curve)

| | SK-OV-3 | | |
|---|---|---|---|
| Compound No. | IC50 (μM) | 95% Confidence Interval (μM) | $R^2$ |
| Foretinib | 17.23 | 11.85 to 25.04 | 0.7477 |
| For-Oxide | 11.6 | 8.971 to 15.01 | 0.8846 |
| For-Methyl | No inhibition | / | / |
| Compound 10 | 7.849 | 5.925 to 10.40 | 0.8928 |
| Compound 5 | 3.494 | 3.155 to 3.869 | 0.9645 |

TABLE 6

Figure 6:
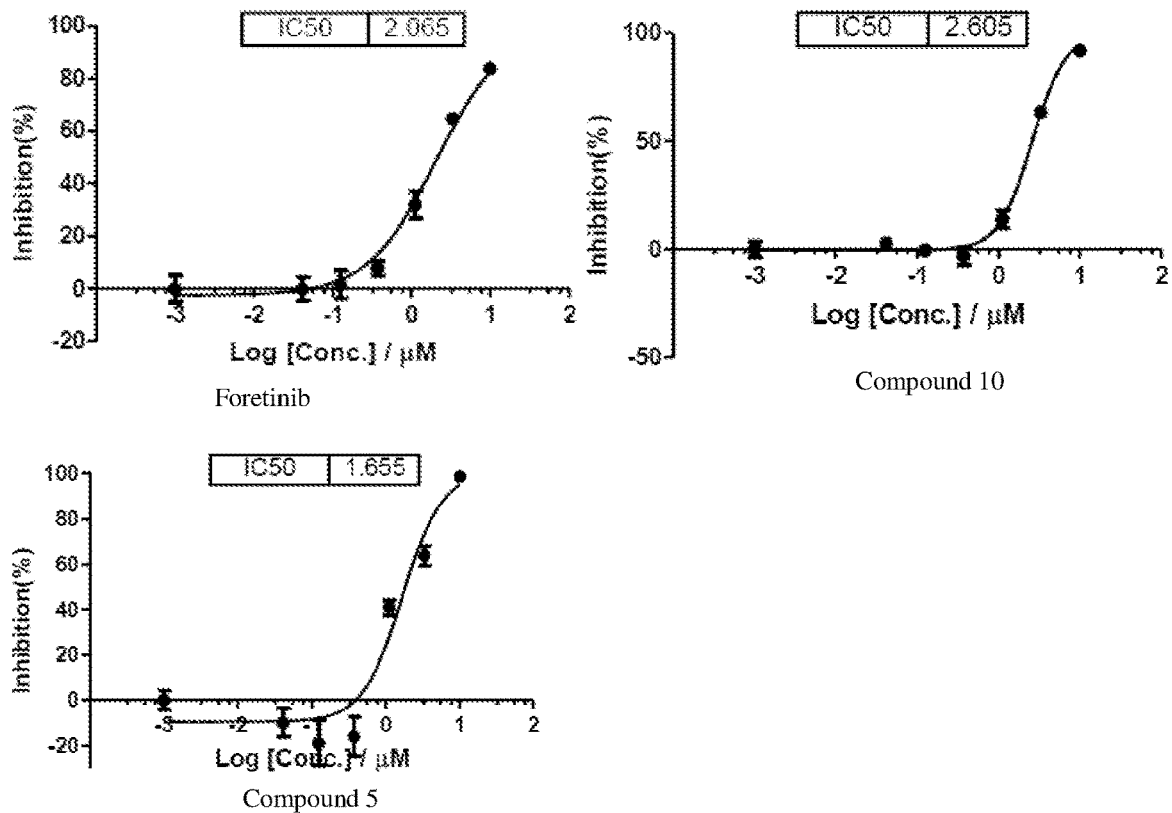
FIG. 6 is the fitted curve for the inhabitation on the proliferation of human colon cancer cells HCT116 in Example 10 of the invention.
Figure 7:
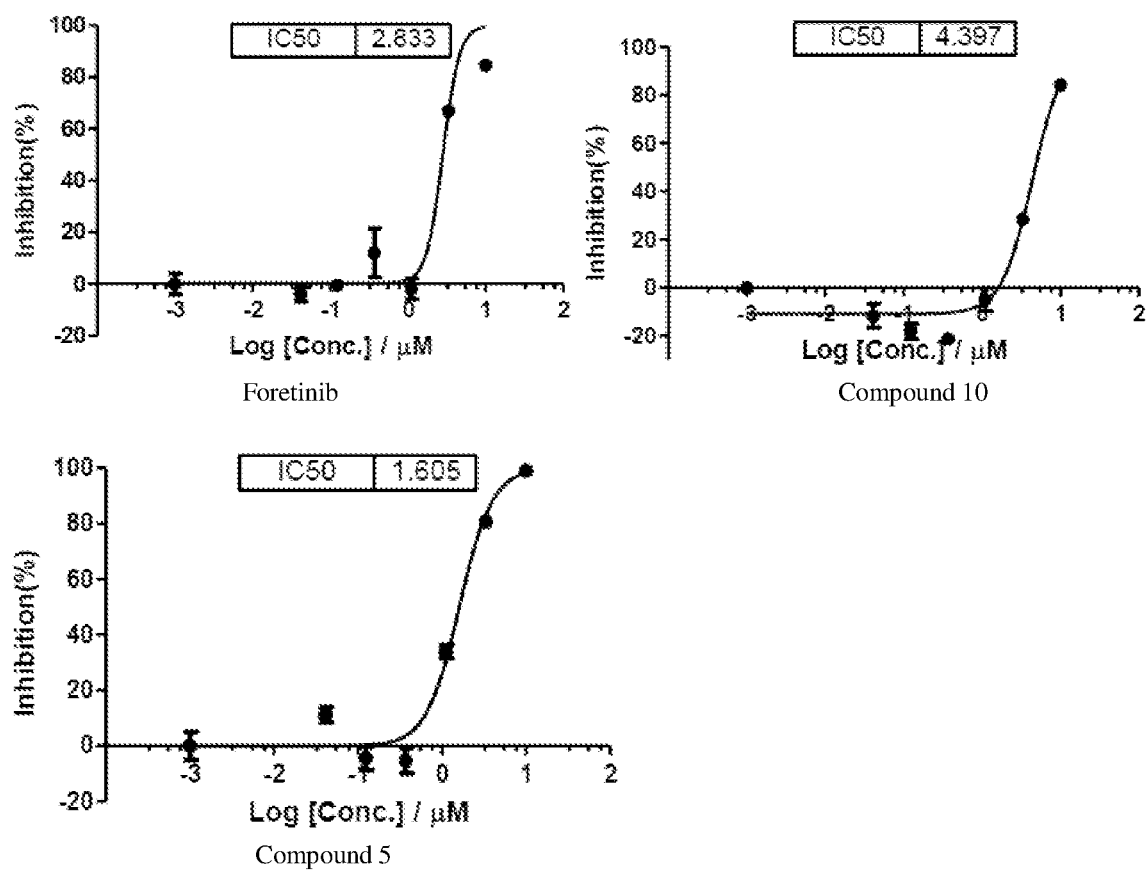
FIG. 7 is the fitted curve for the inhabitation on the proliferation of human lung adenocarcinoma cells A549 in Example 10 of the invention.

Results of Inhibition on the Proliferation of Human Colon Cancer Cells HCT116 and Human Lung Adenocarcinoma Cells A549 (see FIG. 6 and FIG. 7 for the corresponding fitted curves)

| | HCT116 | | | A549 | | |
|---|---|---|---|---|---|---|
| | IC50 (μM) | 95% Confidence Interval (μM) | $R^2$ | IC50 (μM) | 95% Confidence Interval (μM) | $R^2$ |
| Foretinib | 2.065 | 1.542 to 2.763 | 0.9391 | 2.833 | 2.167 to 3.704 | 0.9287 |
| For-Oxide | 3.103 | 2.242 to 4.295 | 0.9149 | 4.921 | 3.965 to 6.107 | 0.9051 |
| For-Methyl | No inhibition | / | / | No inhibition | / | / |
| Compound 10 | 2.605 | 2.262 to 3.001 | 0.9713 | 4.397 | 3.676 to 5.259 | 0.9372 |
| Compound 5 | 1.655 | 1.163 to 2.356 | 0.8922 | 1.605 | 2.350 to 3.477 | 0.9527 |

It can be known from the data of Tables 3-6 that the compounds of the invention can effectively inhibit the proliferation of various cancer cells, such as human lung adenocarcinoma cells, human gastric cancer cells, human colon cancer cells, human ovarian cancer cells, human malignant glioma cells, etc. by inhibiting the activities of tyrosine kinases of C-MET, KDR, etc., and they are especially suitable for treating cancers.

The above embodiments only express the modes of execution of the invention, they are described more specifically and in details, but they can't be understood as the limitation to the scope of the patent of the invention. It shall be indicated that for those skilled in the art, without separating from the idea of the invention, several transformations and improvements can also be obtained, and all these belong to the protective scope of the invention. Therefore, the protective scope for the patent of the invention shall be subject to the claims attached.

The invention claimed is:

1. A compound of formula of (I)

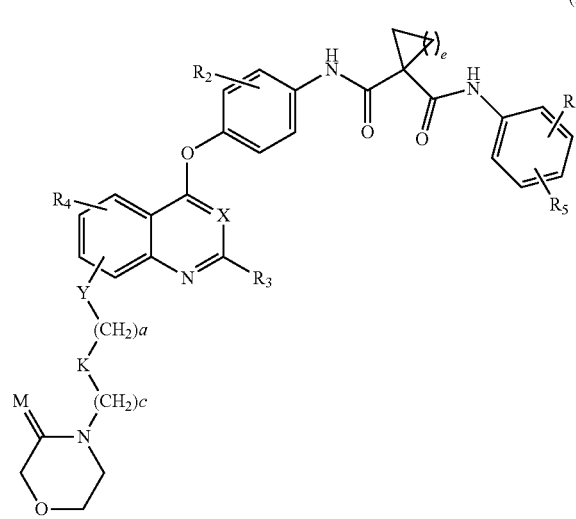

(I)

or a pharmaceutically acceptable salt thereof, wherein, K is selected from the group consisting of

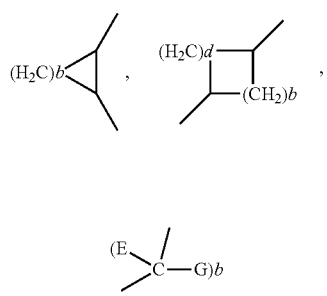

and N—$R_6$; b and d are 1, 2, 3 or 4; E and G are one of hydrogen, halogen, hydroxy, alkoxy, ketone, sulfydryl and alkyl sulfydryl, but E and G cannot be hydrogen at the same time; $R_6$ is one of hydrogen, halo alkyl, halogenated cycloalkyl, alkyl and cycloalkyl;

$R_1$, $R_2$, $R_3$, $R_4$ and $R_5$ are one or several of hydrogen, halogen, halo alkyl, halogenated cycloalkyl, alkyl, cycloalkyl, hydroxy, alkoxy, cycloalkoxy, alkenyl and alkynyl, respectively;

X is one of C—R, C—(CN) and N, and R is one of hydrogen, halogen, halo alkyl, halogenated cycloalkyl, alkyl, cycloalkyl, hydroxy, alkoxy, cycloalkoxy, alkenyl and alkynyl;

Y is one of O, S and N—$R_6$ or is null, and M is O or null;

a and c represent 0, 1, 2 or 3, respectively; and e is 1 or 2.

2. The compound according to claim 1, wherein at least one of said E and G is F.

3. The compound according to claim 1, wherein said Y is O or null.

4. A compound selected from the group consisting of:

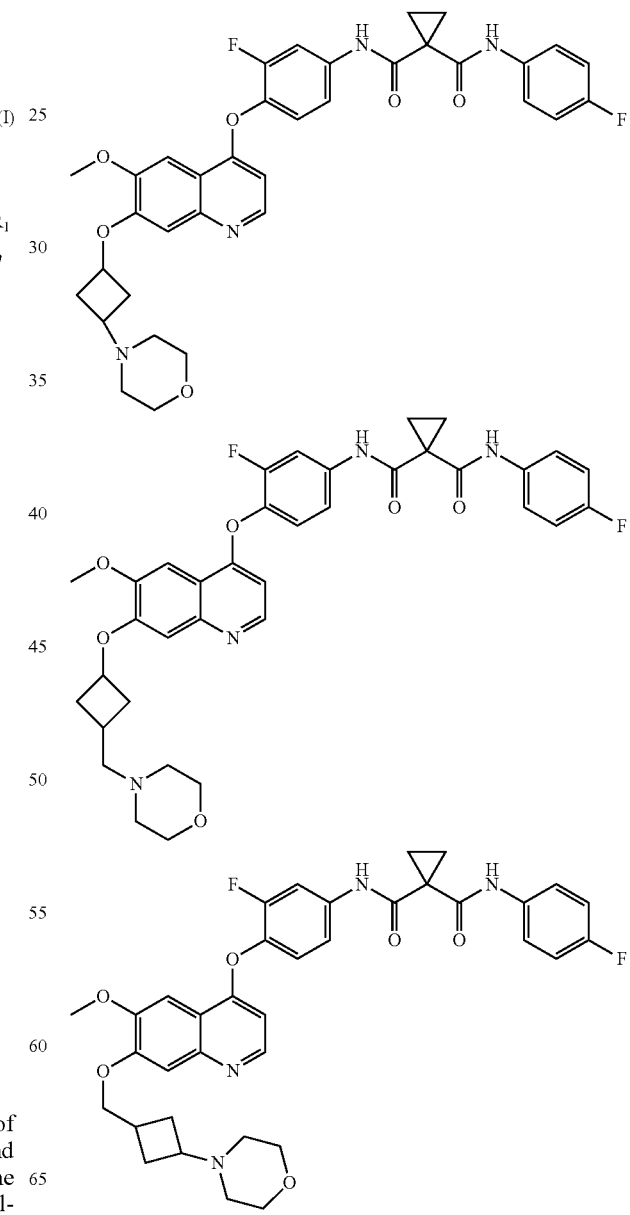

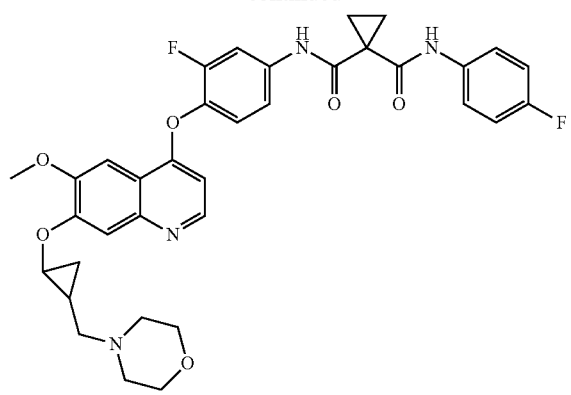
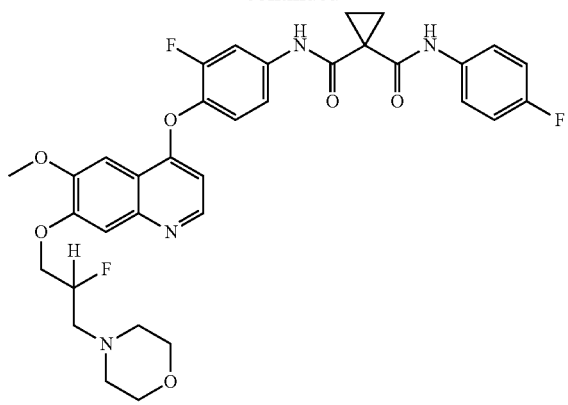
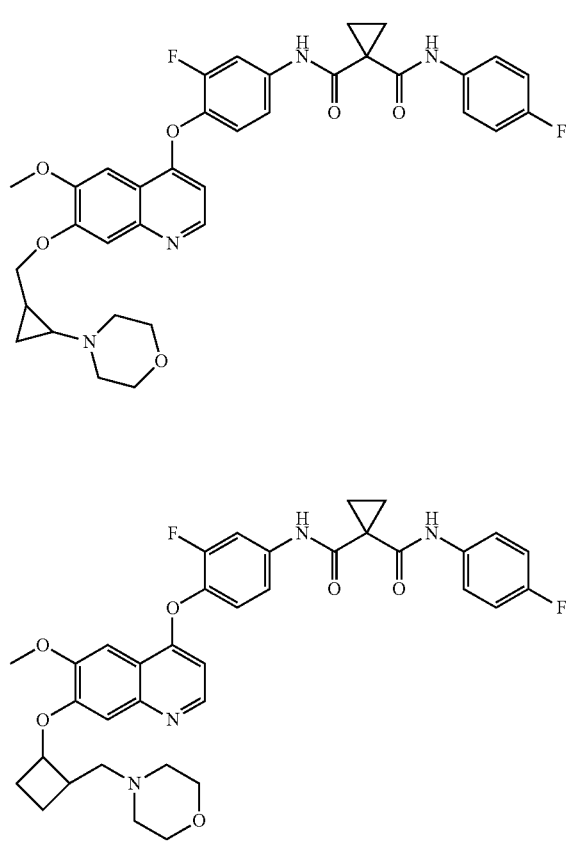
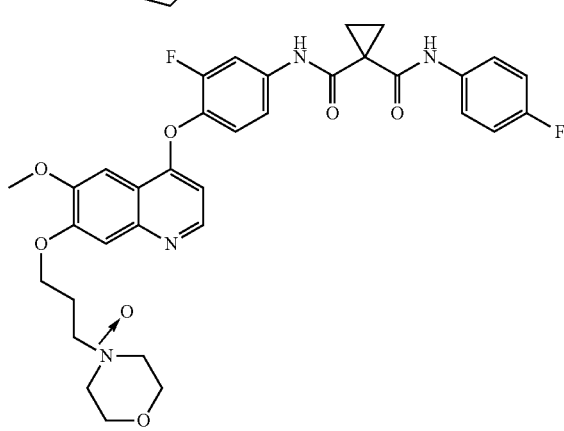
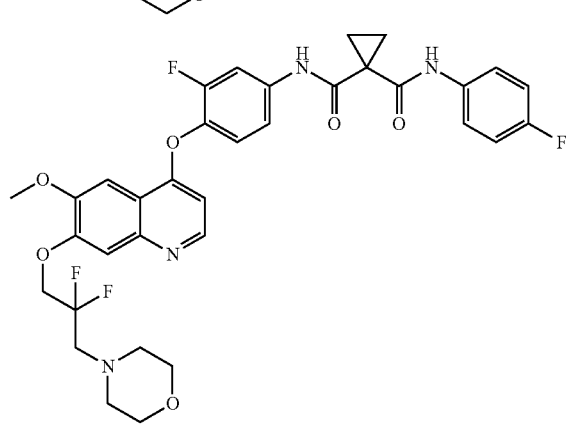
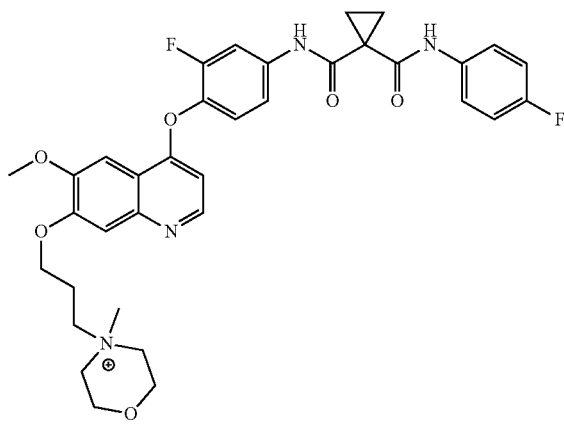

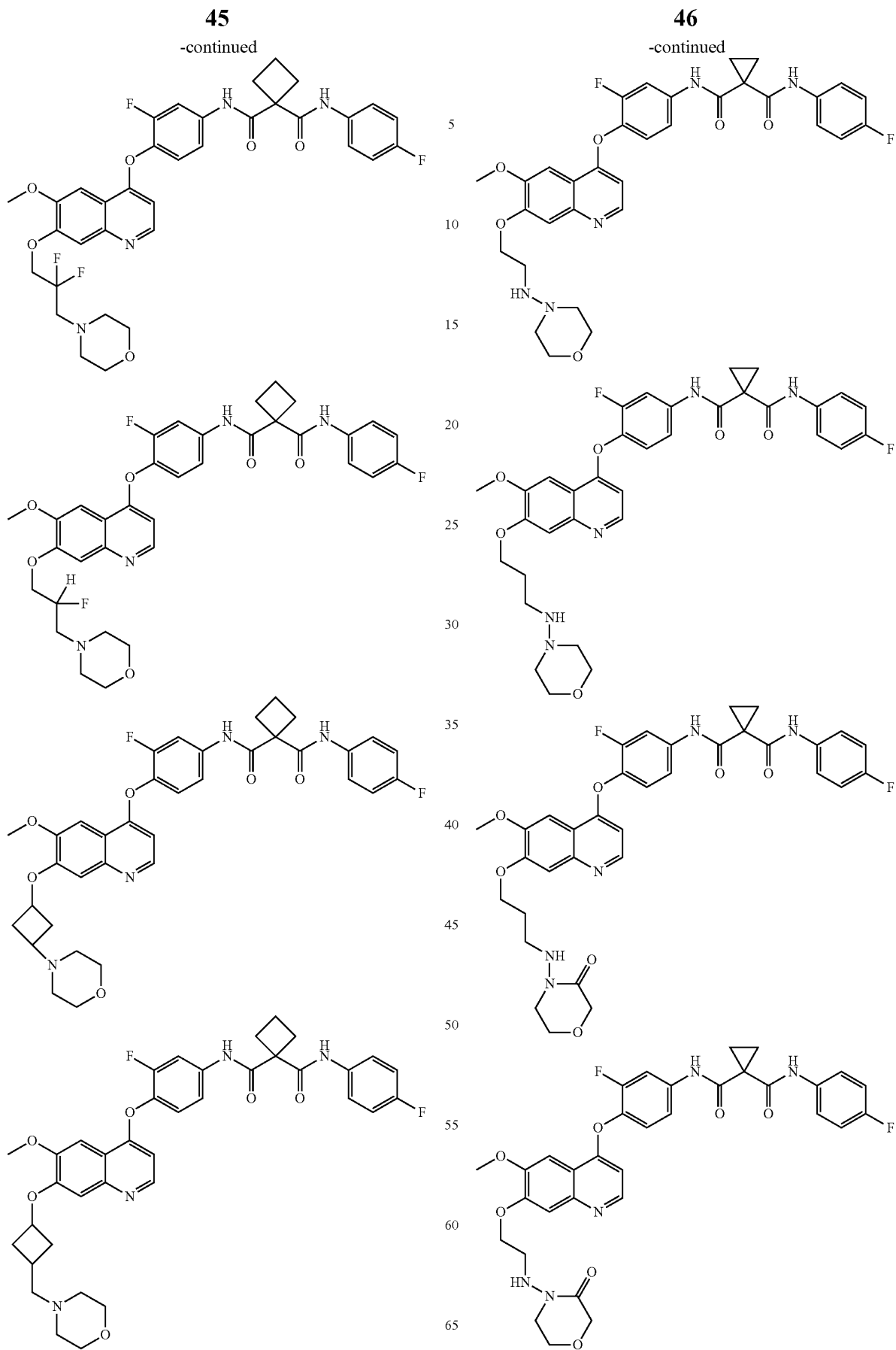

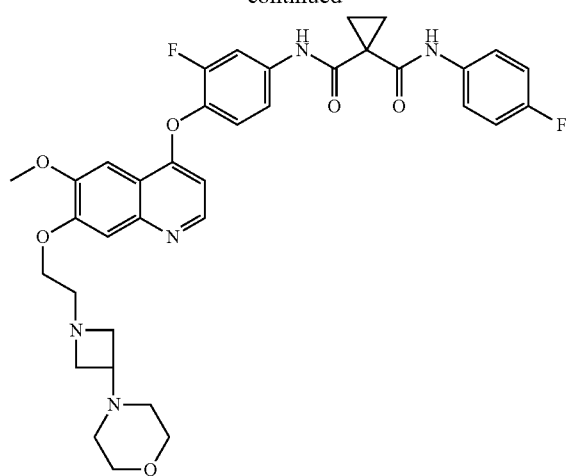
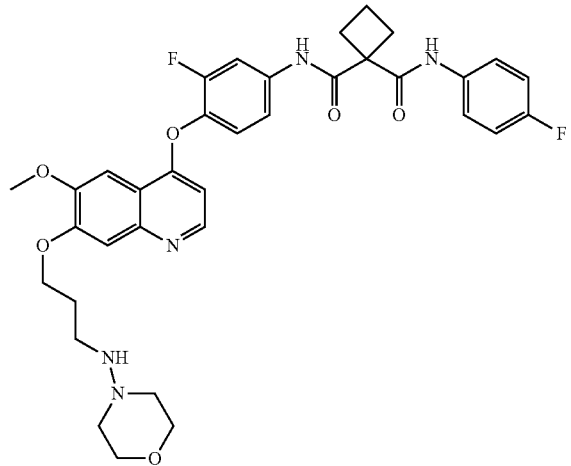
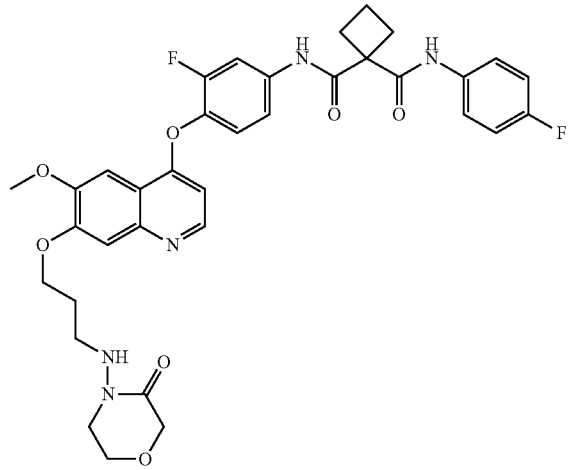
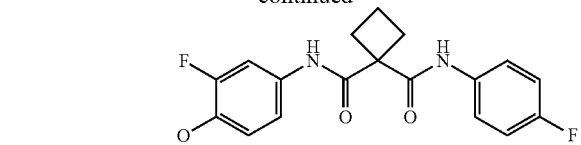
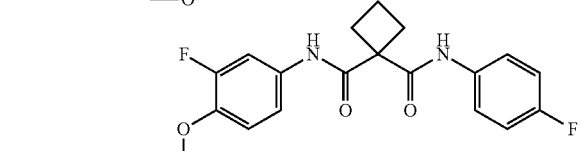
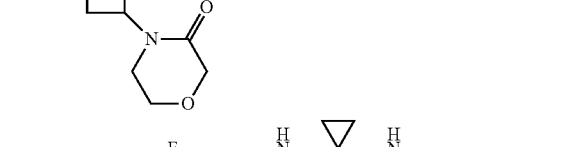
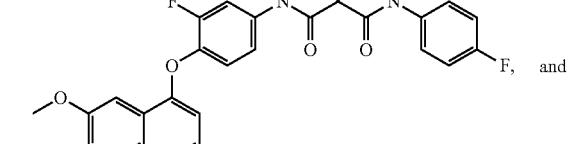
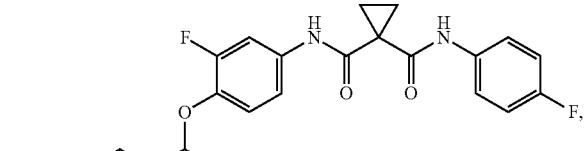
or a pharmaceutically acceptable salt thereof.

5. A pharmaceutical composition, wherein the composition comprises a safe and effective amount of the compound of claim 1 and a pharmaceutically acceptable carrier.

6. A method of inhibiting a tyrosine kinase in a subject in need thereof, comprising administering to the subject the compound of claim 1, wherein the tyrosine kinase comprises at least one of C-MET and KDR.

7. A method of treating cancers in a subject in need thereof, comprising administering to the subject the compound according to claim 1, wherein the cancers comprise lung cancer, gastric cancer, ovarian cancer, colon cancer, pancreatic cancer, adenocarcinoma of esophagus, and malignant glioma.

8. A pharmaceutical composition, wherein the composition comprises a safe and effective amount of the compound of claim 4 and a pharmaceutically acceptable carrier.

9. A method of inhibiting a tyrosine kinase in a subject in need thereof, comprising administering to the subject the compound of claim 4, wherein the tyrosine kinase comprises at least one of C-MET and KDR.

10. A method of treating cancers in a subject in need thereof, comprising administering to the subject the compound according to claim 4, wherein the cancers comprise lung cancer, gastric cancer, ovarian cancer, colon cancer, pancreatic cancer, adenocarcinoma of esophagus, and malignant glioma.

* * * * *